(12) United States Patent
Haap et al.

(10) Patent No.: US 6,967,215 B2
(45) Date of Patent: Nov. 22, 2005

(54) TETRAHYDROCARBAZOLES, A PROCESS FOR THE PREPARATION OF THOSE COMPOUNDS, AND THE USE THEREOF

(75) Inventors: Wolfgang Haap, Lörrach (DE); Andreas Mehlin, Rheinfelden (DE); Karin Petzold, Fischingen (DE); Dietmar Ochs, Schopfheim (DE); Werner Hölzl, Eschentzwiller (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 131 days.

(21) Appl. No.: 10/380,573

(22) PCT Filed: Sep. 11, 2001

(86) PCT No.: PCT/EP01/10479

§ 371 (c)(1),
(2), (4) Date: Mar. 13, 2003

(87) PCT Pub. No.: WO02/24699

PCT Pub. Date: Mar. 28, 2002

(65) Prior Publication Data

US 2004/0097535 A1 May 20, 2004

(30) Foreign Application Priority Data

Sep. 18, 2000 (EP) .......................... 008108441
May 9, 2001 (CH) ................................ 84301

(51) Int. Cl.[7] .................. A61K 31/403; A61K 7/40; C07D 487/02
(52) U.S. Cl. .................. 514/410; 548/418; 548/423; 548/448; 424/405; 546/48; 546/64; 546/70; 546/85; 514/280; 514/285; 514/287; 514/292; 514/411
(58) Field of Search ............... 424/405; 514/410, 514/411, 280, 285, 287, 292; 548/418, 423, 448; 546/48, 64, 70, 85

(56) References Cited

U.S. PATENT DOCUMENTS 5,645,988 A   7/1997   Vande Woude et al. ......... 435/6

FOREIGN PATENT DOCUMENTS

CH         653675       1/1986

OTHER PUBLICATIONS

W. Noland et al., Tetrahedron, vol. 52, No. 13, pp. 4555–4572, (1996).
W. Noland et al., J. Heterocyclic Chem., vol. 30, (1993), pp. 81–91.
K. Diker et al., Tetrahedron Letters, vol. 40, (1999), pp. 7463–7467.
Chem. Abstr. 131:129927 for W. Noland et al., J. Chem. Crystallogr. (1999), 29(1), pp. 9–14.
Chem Abstr. 130:110128 for H.–C. Shi, Youji Huaxue (1998), 18(6), pp. 567–571.
B. Saroja et al., Synthesis Communications, (1986), pp. 748–749.
Chem Abstr. 117:204650 for K. Paull et al, Cancer Res. (1992), 52(14), pp. 3892–3900.
Chem. Abstr. 81:151901 for S. Hiremath et al., Indian Journal of Chemistry, (1974), 12(5), pp. 493–495.
Chem. Abstr. 83:142457 for S. Hiremath et al., J. Karnatak Univ., Sci. (1974), 19, pp. 208–215.
The Merck Index, An Encyclopedia of Chemicals, Drugs and Biologicals, 11th Edition, p. CI–44, (1989).

*Primary Examiner*—Charanjit S. Aulakh
(74) *Attorney, Agent, or Firm*—Kevin T. Mansfield

(57) ABSTRACT

Tetrahydrocarbazoles of formula

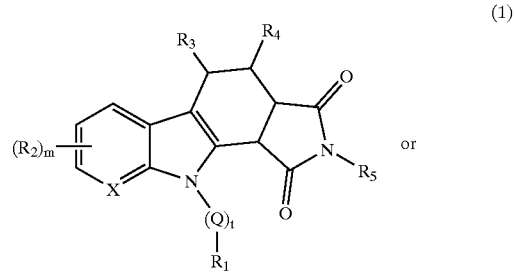

(1)

or

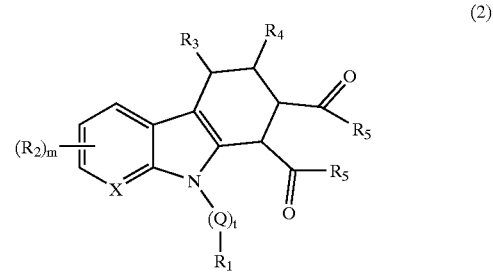

(2)

where Q is $-SO_2-$; $-O-$; or $-(CO)-$; X is $-(CH)-$; or $-N-$; m is from 1 to 3; t is 0 or 1 and the remaining substituents are as defined herein, are useful as antimicrobial active ingredients.

25 Claims, No Drawings

TETRAHYDROCARBAZOLES, A PROCESS FOR THE PREPARATION OF THOSE COMPOUNDS, AND THE USE THEREOF

The present invention relates to novel tetrahydrocarbazoles, to a process for the preparation of those compounds and to the use thereof as antimicrobial active ingredients.

The tetrahydrocarbazoles according to the invention correspond to formula

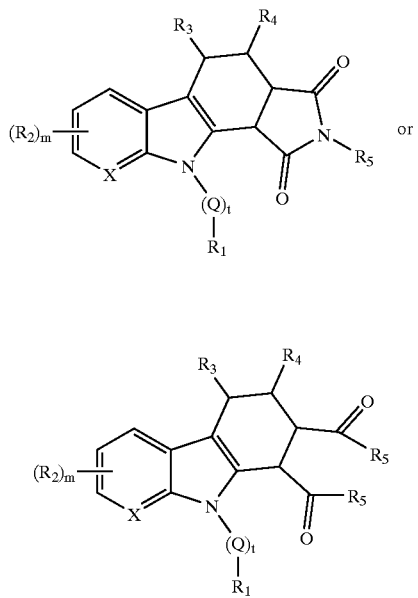

wherein
$R_1$ is hydrogen; $C_1-C_{20}$alkyl; $C_3-C_{12}$cycloalkyl; $C_2-C_{20}$alkenyl; $C_4-C_{12}$cycloalkenyl; $C_3-C_{20}$-alkynyl; $C_4-C_{12}$cycloalkynyl; phenyl or phenyl-$C_1-C_5$alkyl each unsubstituted or substituted by $C_1-C_5$alkyl, $C_3-C_{12}$cycloalkyl, $C_1-C_5$alkoxy, $C_3-C_{12}$cycloalkoxy, halogen, carboxy, $C_1-C_7$alkylcarbonyl, $C_1-C_7$alkoxycarbonyl, $C_3-C_{12}$cycloalkylcarbonyl, $C_3-C_{12}$-cycloalkoxycarbonyl, cyano, trifluoromethyl, pentafluoroethyl, amino, N,N-mono- or di-$C_1-C_{20}$alkylamino or by nitro, $R_2$ is hydrogen; hydroxy; $C_1-C_{20}$alkyl; $C_3-C_{12}$cycloalkyl; $C_1-C_{20}$hydroxyalkyl; $C_1-C_{20}$-hydroxyalkoxy; $C_1-C_{20}$aminoalkyl; N—$C_1-C_{20}$monoalkylamino-$C_1-C_{20}$alkyl; N—$C_1-C_{20}$-monoalkylaminohydroxy-$C_1-C_{20}$alkoxy; N,N—$C_1-C_{20}$dialkylamino-$C_1-C_{20}$alkyl; N,N—$C_1-C_{20}$dialkylaminohydroxy-$C_1-C_{20}$alkoxy; carboxy; carboxy-$C_1-C_{20}$alkyl ester; $C_1-C_{20}$-haloalkyl; $C_1-C_{20}$haloalkoxy; $C_2-C_{20}$alkenyl; $C_4-C_{12}$cycloalkenyl; $C_3-C_{20}$alkynyl; $C_4-C_{12}$-cycloalkynyl; $C_1-C_{20}$alkoxy; $C_2-C_{20}$alkenyloxy; $C_2-C_{20}$alkynyloxy; halogen; cyano; $C_1-C_7$alkylcarbonyl; nitro; trifluoromethyl; or pentafluoroethyl;

$R_3$ and $R_4$ are each independently of the other hydrogen; or $C_1-C_{20}$alkyl; or $R_3$ and $R_4$ together denote a $C_2-C_{20}$alkylene radical; a $C_2-C_{20}$alkenylene radical; a $C_4-C_{20}$-alkynylene radical; or a $C_3-C_{20}$alkylene radical interrupted by —N($R_6$)—, it being possible for such bivalent radicals to be further substituted by one or more $C_1-C_{20}$alkyl, $C_3-C_{12}$-cycloalkyl, $C_2-C_{20}$alkenyl, $C_4-C_{12}$cycloalkenyl, $C_3-C_{20}$alkynyl, $C_4-C_{12}$cycloalkynyl, $C_1-C_7$-alkoxycarbonyl, or phenyl or phenyl-$C_1-C_5$alkyl each unsubstituted or substituted by $C_1-C_5$alkyl, $C_3-C_{12}$cycloalkyl, $C_1-C_5$alkoxy, $C_3-C_{12}$cycloalkoxy, halogen, carboxy, $C_1-C_7$alkoxycarbonyl, $C_3-C_{12}$cycloalkoxycarbonyl, cyano, trifluoromethyl, pentafluoroethyl, amino, N,N-mono- or di-$C_1-C_{20}$alkylamino or by nitro; or $R_3$ and $R_4$ together denote a bicyclo[x.y.z.]$C_4-C_{20}$alkylene; or bicyclo[x.y.z.]$C_4-C_{20}$alkylene interrupted by —N($R_6$)—, wherein x, y and z are each independently of the others from 0 to 10;

$R_5$ is hydrogen; hydroxy; $C_1-C_{20}$alkyl; $C_1-C_{20}$alkoxy; $C_3-C_{12}$cycloalkyl; $C_2-C_{20}$alkenyl; $C_4-C_{12}$cycloalkenyl; $C_3-C_{20}$alkynyl; $C_4-C_{12}$cycloalkynyl; phenyl or phenyl-$C_1-C_5$alkyl each unsubstituted or substituted by $C_1-C_5$alkyl, $C_3-C_{12}$cycloalkyl, $C_1-C_5$alkoxy, $C_3-C_{12}$-cyclolkoxy, halogen, carboxy, $C_1-C_7$alkoxycarbonyl, $C_3-C_{12}$cycloalkoxycarbonyl, cyano, triluoroethyl, pentafluoroethyl, amino, N,N-mono- or di-$C_1-C_{20}$alkylamino or by nitro;

$R_6$ is hydrogen; $C_1-C_{20}$alkyl; $C_3-C_{12}$cycloalkyl; $C_2-C_{20}$alkenyl; $C_4-C_{12}$cycloalkenyl; $C_3-C_{20}$-alkynyl; $C_4-C_{12}$cycloalkynyl; $C_1-C_7$alkoxycarbonyl; phenyl or phenyl-$C_1-C_5$alkyl each unsubstituted or substituted by $C_1-C_5$alkyl, $C_3-C_{12}$cycloalkyl, $C_1-C_5$alkoxy, $C_3-C_{12}$-cyclolkoxy, halogen, carboxy, $C_1-C_7$alkoxycarbonyl, $C_3-C_{12}$cycloalkoxycarbonyl, cyano, trifluoromethyl, pentafluoroethyl, amino, N,N-mono- or di-$C_1-C_{20}$alkylamino or by nitro;

Q is —$SO_2$—; —O—; or —(CO)—;
X is —CH—; or —N—;
m is from 1 to 3; and
t is 0 or 1.

$C_1-C_{20}$Alkyl denotes straight-chain or branched alkyl radicals, such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_3-C_{12}$Cycloalkyl is, for example, cyclopropyl, cyclobutyl, cyclopentyl, cycloheptyl, cyclooctyl, cyclononyl, cyclodecyl, cycloundecyl, cyclodocecyl and especially cyclohexyl.

Within the scope of the meanings given, alkenyl includes inter alia allyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-dodec-2-enyl or n-octadec-4-enyl.

$C_1-C_{20}$Alkoxy denotes straight-chain or branched radicals, such as methoxy, ethoxy, propoxy, butoxy or pentyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy, octadecyloxy or eicosyloxy.

Halogen is fluorine, chlorine, bromine or iodine.

Preference is given to the use of compounds of formula (1) or (2) wherein
$R_1$ is hydrogen; $C_1-C_{20}$alkyl; $C_3-C_{12}$cycloalkyl; $C_2-C_{20}$alkenyl; $C_4-C_{12}$cycloalkenyl; $C_3-C_{20}$-alkynyl; $C_4-C_{12}$cycloalkynyl; phenyl or phenyl-$C_1-C_5$alkyl each unsubstituted or substituted by $C_1-C_5$alkyl, $C_3-C_{12}$cycloalkyl, $C_1-C_5$alkoxy, $C_3-C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxyarbonyl, cyano, trifluoromethyl, pentafluoroethyl, amino, N,N-mono- or di-$C_1$–$C_{20}$alkylmino or by nitro, $R_2$ is hydrogen; hydroxy; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$alkoxy; $C_2$–$C_{20}$alkenyloxy; $C_2$–$C_{20}$alkynyloxy; halogen cyano; $C_1$–$C_7$alkylcarbonyl; nitro; trifluoromethyl; or pentafluoroethyl;

$R_3$ and $R_4$ are each independently of the other hydrogen; or $C_1$–$C_{20}$alkyl; or $R_3$ and $R_4$ denote a $C_2$–$C_{20}$alkylene radical; a $C_2$–$C_{20}$alkenylene radical; a $C_4$–$C_{20}$alkynylene radical; or a $C_3$–$C_{20}$alkylene radical interrupted by —N($R_6$)—, it being possible for such bivalent radicals to be further substituted by one or more $C_1$–$C_{20}$alkyl, $C_3$–$C_{12}$cycloalkyl, $C_2$–$C_{20}$-alkenyl, $C_4$–$C_{12}$cycloalkenyl, $C_3$–$C_{20}$alkynyl, $C_4$–$C_{12}$cycloalkynyl, $C_1$–$C_7$alkoxycarbonyl, or phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

$R_5$ is hydrogen; hydroxy; $C_1$–$C_{20}$alkyl; $C_1$–$C_{20}$alkoxy; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$-cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$-cycloalkoxy, halogen, carboxy, $C_1$–$C_7$alkoxycarbonyl, $C_3$–$C_{12}$cycloalkoxycarbonyl, cyano, trifluorom thyl, pentafluoroethyl, amino, N,N-mono- or di-$C_1$–$C_{20}$alkylamino or by nitro;

Q is —$SO_2$—; —O—; or —(CO)—;

X is —CH—; or —N—;

m is from 1 to 3; and t is 0 or 1.

In formula (1)

$R_1$ is preferably hydrogen; $C_1$–$C_{20}$alkyl; phenyl or phenyl-$C_1$–$C_5$alkyl, and is especially hydrogen; or $C_1$–$C_5$alkyl.

Preference is given also to compounds of formula (1) wherein $R_2$ is hydrogen; $C_1$–$C_{20}$alkyl; $C_1$–$C_{20}$alkoxy; or halogen and is especially hydrogen; $C_1$–$C_5$alkyl; $C_1$–$C_5$alkoxy; or halogen.

Very special preference is given to compounds of formula

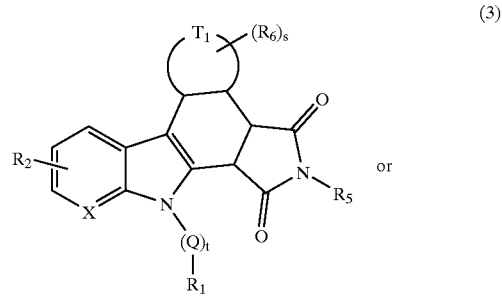

(3)

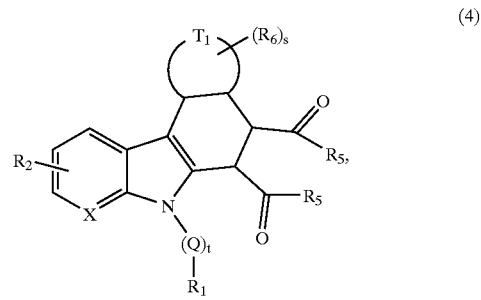

(4)

wherein $R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxyarbonyl, cyano, trifluoromethyl, pentafluoroethyl, amino, N,N-mono- or di-$C_1$–$C_{20}$alkylmino or by nitro, $R_2$ is hydrogen; hydroxy; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_5$ is hydrogen; hydroxy; $C_1$–$C_{20}$alkyl; $C_1$–$C_{20}$alkoxy; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$-cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkeny; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_7$alkyl, $C_3$–$C_{12}$cycloalkyl, $C_1$–$C_5$alkoxy, $C_3$–$C_{12}$-cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

Q is —$SO_2$—; —O—; or —(CO)—;

$T_1$ is $C_2$–$C_{20}$calkylene; $C_2$–$C_{20}$alkenylene; $C_4$–$C_{20}$alkynylene; or $C_3$–$C_{20}$alkylene interrupted by

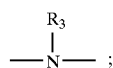

X is —CH—; or —N—;
s is from 1 to 4; and
t is 0 or 1.

Preference is given to compounds of formula (3) or (4) wherein
$T_1$ is a —(CH$_2$)$_{2-12}$— radical and
$R_6$ is hydrogen; or $C_1$–$C_5$alkyl,
and especially to compounds of formula (3) or (4) wherein
$T_1$ is a —(CH$_2$)$_3$—, —(CH$_2$)$_4$—, —(CH$_2$)$_5$—, or —(CH$_2$)$_{10}$— radical; and
$R_6$ is hydrogen; or $C_1$–$C_5$alkyl.
$R_5$ in formula (1) is preferably hydrogen; $C_1$–$C_{20}$alkyl; phenyl or phenyl-$C_1$–$C_5$alkyl; and more especially hydrogen; $C_1$–$C_5$alkyl; or phenyl.

More especially preferred compounds according to the invention correspond to formula

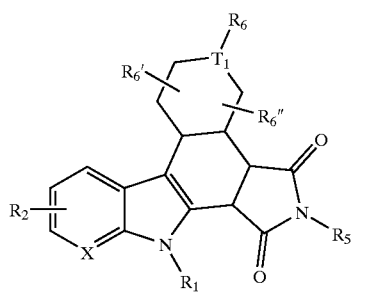

(5)

or

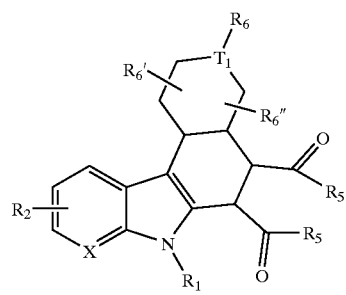

(6)

wherein
$R_6'$ and $R_6''$ are each independently of the other hydrogen; $C_1$–$C_{20}$alkyl; $C_1$–$C_7$alkoxy-carbonyl; phenyl or phenyl-$C_1$–$C_5$alkyl each unsubstituted or substituted by $C_1$–$C_5$alkyl, $C_1$–$C_7$alkoxycarbonyl, N,N-mono- or di-$C_1$–$C_{20}$alkylamino or by nitro;
$T_1$ is

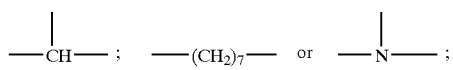

and
$R_1$, $R_2$, $R_5$, $R_6$ and X are as defined for formula (3).
In formulae (5) and (6) preferably $R_6'$, $R_6''$ and $R_6$ are each independently of the others hydrogen; $C_1$–$C_{20}$alkyl; $C_1$–$C_7$-alkoxycarbonyl; phenyl; or phenyl-$C_1$–$C_5$alkyl.

Special preference is given to compounds of formula (5) and (6) wherein $R_6'$ and $R_6''$ and $R_6$ are each independently of the others hydrogen; $C_1$–$C_5$alkyl; $C_1$–$C_7$-alkoxycarbonyl; phenyl or benzyl.

Further preferred compounds according to the invention correspond to formula

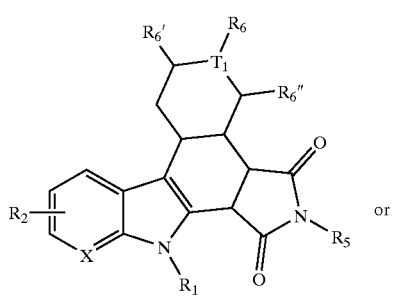

(7)

or

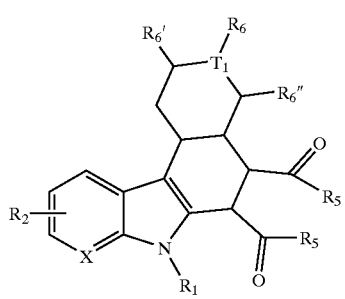

(8)

wherein $R_1$ is hydrogen; or $C_1$–$C_5$alkyl;

$R_2$ is hydrogen; $C_1$–$C_4$alkyl; Cl or Br;

$R_5$ is hydrogen; $C_1$–$C_5$alkyl; or phenyl $R_6'$ and $R_6''$ are each independently of the other hydrogen, $C_1$–$C_5$alkyl; or $C_1$–$C_7$alkoxy-carbonyl;

$R_6$ is hydrogen; $C_1$–$C_5$alkyl; $C_1$–$C_7$alkylcarbonyl; or phenyl-$C_1$–$C_5$alkyl;

$T_1$ is

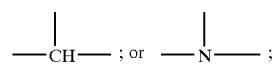

and

X is —CH—.

Compounds according to the invention are listed in Tables 1 a and b below by way of example:

TABLE 1a

General structural formula

| Compound of formula | R₁ | R₂ | R₆ ring | R₅ | Yield [surfaces %] |
|---|---|---|---|---|---|
| 9 | H | H | —(CH₂)₄— | Ph | 92 |
| 10 | H | 7-Br | —(CH₂)₄— | Ph | 75 |
| 11 | Me | H | —(CH₂)₄— | Ph | 68 |
| 12 | H | H | —(CH₂)₃— | Ph | 93 |
| 13 | H | H | 4-tert-butylcyclohexyl | Ph | 67 |
| 14 | H | H | —(CH₂)₅— | Ph | 92 |
| 15 | H | H | N-propylpiperidinyl | Ph | 79 |
| 16 | H | H | —(CH₂)₄— | H | 48 |
| 17 | H | H | —(CH₂)₄— | Et | 55 |
| 18 | H | 7-Br | —(CH₂)₃— | Ph | 96 |
| 19 | H | 7-Br | 4-tert-butylcyclohexyl | Ph | 83 |
| 20 | H | 7-Br | —(CH₂)₅— | Ph | 68 |
| 21 | Me | H | —(CH₂)₃— | Ph | 95 |
| 22 | Me | H | 4-tert-butylcyclohexyl | Ph | 64 |
| 23 | Me | H | —(CH₂)₅— | Ph | 75 |

TABLE 1a-continued

General structural formula

| Compound of formula | R$_1$ | R$_2$ | R$_6$ (ring) | R$_5$ | Yield [surfaces %] |
|---|---|---|---|---|---|
| 24 | Me | H | piperidine with NH, gem-dimethyl groups | Ph | 38 |
| 25 | H | H | —(CH$_2$)$_3$— | H | 86 |
| 26 | H | H | cyclohexyl with t-Bu | H | 95 |
| 27 | H | H | —(CH$_2$)$_5$— | H | 68 |
| 28 | H | H | piperidine with NH, gem-dimethyl groups | H | 88 |
| 29 | H | 7-Br | —(CH$_2$)$_4$— | H | 92 |
| 30 | H | 7-Br | —(CH$_2$)$_3$— | H | 90 |
| 31 | H | 7-Br | cyclohexyl with t-Bu | H | 41 |
| 32 | H | 7-Br | —(CH$_2$)$_5$— | H | 79 |
| 33 | H | 7-Br | N-propyl piperidine | H | 44 |
| 34 | Me | H | —(CH$_2$)$_4$— | H | 77 |
| 35 | Me | H | —(CH$_2$)$_3$— | H | 95 |

TABLE 1a-continued

General structural formula

| Compound of formula | $R_1$ | $R_2$ | $R_6$ (ring) | $R_5$ | Yield [surfaces %] |
|---|---|---|---|---|---|
| 36 | Me | H | 4-tert-butylcyclohexyl | H | 84 |
| 37 | Me | H | —(CH$_2$)$_5$— | H | 87 |
| 38 | H | H | —(CH$_2$)$_3$— | Et | 91 |
| 39 | H | H | 4-tert-butylcyclohexyl | Et | 66 |
| 40 | H | H | —(CH$_2$)$_5$— | Et | 89 |
| 41 | H | H | N-propylpiperidinyl | Et | 57 |
| 42 | H | 7-Br | —(CH$_2$)$_4$— | Et | 85 |
| 43 | H | 7-Br | —(CH$_2$)$_3$— | Et | 90 |
| 44 | H | 7-Br | 4-tert-butylcyclohexyl | Et | 47 |
| 45 | H | 7-Br | —(CH$_2$)$_5$— | Et | 51 |

TABLE 1a-continued
General structural formula
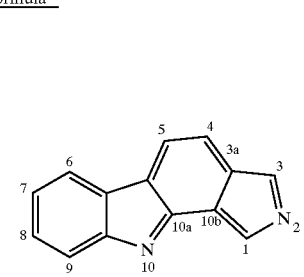
| Compound of formula | R₁ | R₂ | (R₆ ring) | R₅ | Yield [surfaces %] |
|---|---|---|---|---|---|
| 46 | H | 7-Br | N-propyl piperidine | Et | 91 |
| 47 | Me | H | —(CH₂)₄— | Et | 94 |
| 48 | Me | H | —(CH₂)₃— | Et | 95 |
| 49 | Me | H | tert-butyl cyclohexyl | Et | 80 |
| 50 | Me | H | —(CH₂)₅— | Et | 90 |
| 51 | H | 9-Et | —(CH₂)₄— | Ph | 95 |
| 52 | H | H | N-(ethoxycarbonyl) piperidine | Ph | 96 |
| 53 | H | H | isopropyl | Ph | 59 |
| 54 | H | H | N-(ethoxycarbonyl) piperidine | H | 19 |
| 55 | H | H | N-isopropyl piperidine | H | 85 |

TABLE 1a-continued

General structural formula

| Compound of formula | R₁ | R₂ | R₆ (ring) | R₅ | Yield [surfaces %] |
|---|---|---|---|---|---|
| 56 | H | H | (methylcyclohexyl) | H | 44 |
| 57 | H | H | (bicyclic ring system) | H | 65 |
| 58 | H | H | (ethylcyclohexyl) | H | 62 |
| 59 | H | H | (tert-butyl cyclohexyl) | H | 49 |
| 60 | H | H | (N-benzyl piperidinyl) | H | 37 |
| 61 | H | H | —(CH₂)₁₀— | H | 90 |
| 62 | H | H | —(CH₂)₆— | H | 63 |
| 63 | H | H | (trimethylcyclohexyl) | H | 81 |
| 64 | H | H | isopropyl | H | 28 |

TABLE 1a-continued

General structural formula

| Compound of formula | R₁ | R₂ | R₆ | R₅ | Yield [surfaces %] |
|---|---|---|---|---|---|
| 65 | H | H | Me | H | 62 |
| 66 | H | H | Et | H | 58 |
| 67 | H | H | isobutyl | H | 58 |
| 68 | H | 7-Br | N-(ethoxycarbonyl)piperidin-4-yl | H | 93 |
| 69 | H | 7-Br | N-isopropylpiperidin-4-yl | H | 93 |
| 70 | H | 7-Br | 4-methylcyclohexyl | H | 90 |
| 71 | H | 7-Br | 4-propylcyclohexyl | H | 93 |
| 72 | H | 7-Br | 4-tert-pentylcyclohexyl | H | 94 |
| 73 | H | 7-Br | —(CH₂)₆— | H | 33 |

TABLE 1a-continued
General structural formula
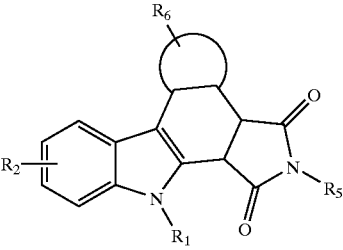
| Compound of formula | R₁ | R₂ | R₆ (ring) | R₅ | Yield [surfaces %] |
|---|---|---|---|---|---|
| 74 | H | 9-Et | —(CH₂)₄— | H | 68 |
| 75 | H | 9-Et | —(CH₂)₃— | H | 91 |
| 76 | H | 9-Et | 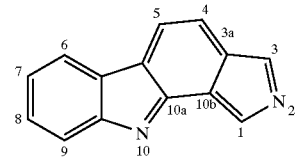 | H | 99 |
| 77 | H | 9-Et | —(CH₂)₅— | H | 93 |
| 78 | H | 9-Et | 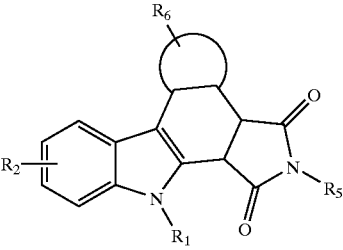 | H | 82 |
| 79 | H | 9-Et | 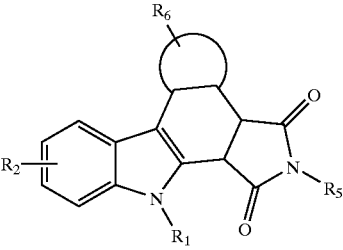 | H | 56 |
| 80 | H | 9-Et | 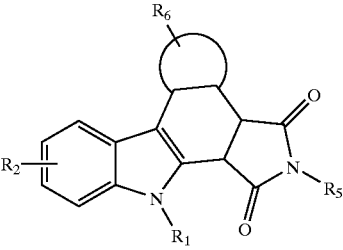 | H | 78 |
| 81 | H | 9-Et | 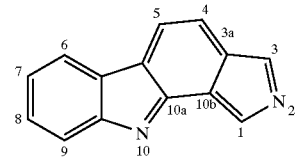 | H | 36 |

TABLE 1a-continued

General structural formula

| Compound of formula | R₁ | R₂ | (R₆ ring) | R₅ | Yield [surfaces %] |
|---|---|---|---|---|---|
| 82 | H | 9-Et | 4-methylcyclohexyl | H | 63 |
| 83 | H | 9-Et | cyclopentyl-cyclohexyl | H | 74 |
| 84 | H | 9-Et | 4-propylcyclohexyl | H | 91 |
| 85 | H | 9-Et | 4-tert-butylcyclohexyl | H | 64 |
| 86 | H | 9-Et | N-ethylpiperidinyl | H | 39 |
| 87 | H | 9-Et | N-benzylpiperidinyl | H | 26 |
| 88 | H | 9-Et | —(CH₂)₁₀— | H | 64 |
| 89 | H | 9-Et | —(CH₂)₆— | H | 86 |

TABLE 1a-continued

General structural formula

| Compound of formula | R₁ | R₂ | R₆ ring | R₅ | Yield [surfaces %] |
|---|---|---|---|---|---|
| 90 | H | 9-Et | 3,3,5,5-tetramethylcyclohexyl | H | 63 |
| 91 | H | 7-MeO | —(CH₂)₄— | H | 93 |
| 92 | H | 7-MeO | —(CH₂)₃— | H | 93 |
| 93 | H | 7-MeO | 4-tert-butylcyclohexyl | H | 56 |
| 94 | H | 7-MeO | —(CH₂)₅— | H | 71 |
| 95 | H | 7-MeO | 2,2,6,6-tetramethylpiperidinyl | H | 10 |
| 96 | H | 7-MeO | N-propylpiperidinyl | H | 88 |
| 97 | H | 7-MeO | N-ethoxycarbonylpiperidinyl | H | 22 |

TABLE 1a-continued

General structural formula

| Compound of formula | R₁ | R₂ | R₆ ring | R₅ | Yield [surfaces %] |
|---|---|---|---|---|---|
| 98 | H | 7-MeO | N-isopropyl piperidinyl | H | 76 |
| 99 | H | 7-MeO | 4-methylcyclohexyl | H | 60 |
| 100 | H | 7-MeO | bicyclic cyclohexyl-cyclopentyl | H | 83 |
| 101 | H | 7-MeO | 4-propylcyclohexyl | H | 94 |
| 102 | H | 7-MeO | 4-tert-butylcyclohexyl | H | 79 |
| 103 | H | 7-MeO | N-ethyl piperidinyl | H | 74 |

TABLE 1a-continued

General structural formula

| Compound of formula | R₁ | R₂ | R₆ ring | R₅ | Yield [surfaces %] |
|---|---|---|---|---|---|
| 104 | H | 7-MeO | piperidine with N-benzyl | H | 84 |
| 105 | H | 7-MeO | N-methylpiperidine | H | 80 |
| 106 | H | 7-MeO | —(CH$_2$)$_{10}$— | H | 93 |
| 107 | H | 7-MeO | —(CH$_2$)$_6$— | H | 34 |
| 108 | H | 7-MeO | 3,3,5,5-tetramethylcyclohexane | H | 27 |
| 109 | H | H | —(CH$_2$)$_4$— | Me | 54 |
| 110 | H | H | —(CH$_2$)$_3$— | Me | 81 |
| 111 | H | H | 4-tert-butylcyclohexane | Me | 98 |
| 112 | H | H | —(CH$_2$)$_5$— | Me | 93 |
| 113 | H | H | 2,2,6,6-tetramethylpiperidine (NH) | Me | 47 |

TABLE 1a-continued

General structural formula

| Compound of formula | R₁ | R₂ | (R₆ ring substituent) | R₅ | Yield [surfaces %] |
|---|---|---|---|---|---|
| 114 | H | H | N-propylpiperidinyl | Me | 86 |
| 115 | H | H | N-ethoxycarbonylpiperidinyl | Me | 16 |
| 116 | H | H | N-isopropylpiperidinyl | Me | 64 |
| 117 | H | H | 4-methylcyclohexyl | Me | 98 |
| 118 | H | H | cyclopentyl-cyclohexyl fused | Me | 87 |
| 119 | H | H | 4-propylcyclohexyl | Me | 98 |

TABLE 1a-continued

General structural formula

| Compound of formula | $R_1$ | $R_2$ | $R_6$ (ring) | $R_5$ | Yield [surfaces %] |
|---|---|---|---|---|---|
| 120 | H | H | 4-(tert-pentyl)cyclohexyl | Me | 98 |
| 121 | H | H | 1-ethylpiperidin-4-yl | Me | 83 |
| 122 | H | H | 1-benzylpiperidin-4-yl | Me | 93 |
| 123 | H | H | 1-methylpiperidin-4-yl | Me | 89 |
| 124 | H | H | —(CH$_2$)$_{10}$— | Me | 95 |
| 125 | H | H | —(CH$_2$)$_6$— | Me | 43 |
| 126 | H | H | 3,3,5,5-tetramethylcyclohexyl | Me | 98 |
| 127 | H | 7-Br | —(CH$_2$)$_4$— | Me | 92 |
| 128 | H | 7-Br | —(CH$_2$)$_3$— | Me | 94 |

TABLE 1a-continued
General structural formula
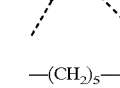
| Compound of formula | $R_1$ | $R_2$ | 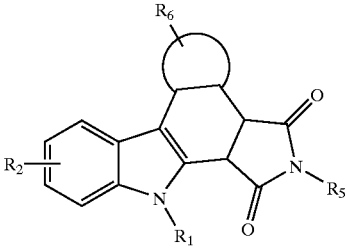 | $R_5$ | Yield [surfaces %] |
|---|---|---|---|---|---|
| 129 | H | 7-Br | 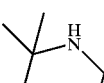 | Me | 99 |
| 130 | H | 7-Br | —(CH$_2$)$_5$— | Me | 76 |
| 131 | H | 7-Br | 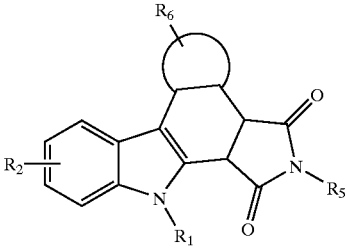 | Me | 69 |
| 132 | H | 7-Br |  | Me | 97 |
| 133 | H | 7-Br | 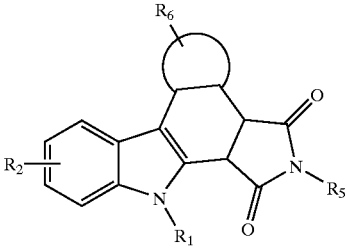 | Me | 22 |
| 134 | H | 7-Br | 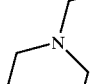 | Me | 92 |
| 135 | H | 7-Br | 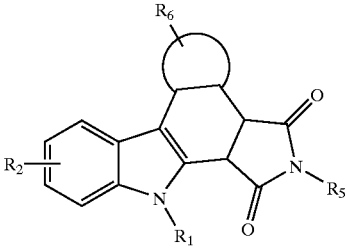 | Me | 95 |

TABLE 1a-continued

General structural formula

| Compound of formula | R₁ | R₂ | $R_6$ ring | R₅ | Yield [surfaces %] |
|---|---|---|---|---|---|
| 136 | H | 7-Br | cyclohexyl-cyclopentyl | Me | 69 |
| 137 | H | 7-Br | 4-propylcyclohexyl | Me | 84 |
| 138 | H | 7-Br | 4-tert-butylcyclohexyl | Me | 75 |
| 139 | H | 7-Br | 1-ethylpiperidin-4-yl | Me | 87 |
| 140 | H | 7-Br | 1-benzylpiperidin-4-yl | Me | 16 |
| 141 | H | 7-Br | 1-methylpiperidin-4-yl | Me | 73 |
| 142 | H | 7-Br | —(CH₂)₁₀— | Me | 81 |
| 143 | H | 7-Br | —(CH₂)₆— | Me | 97 |

TABLE 1a-continued
General structural formula
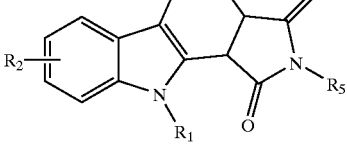
| Compound of formula | R₁ | R₂ | R₆ ring | R₅ | Yield [surfaces %] |
|---|---|---|---|---|---|
| 144 | H | 7-Br | 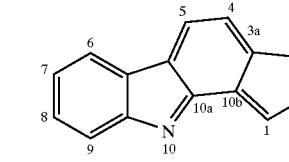 | Me | 92 |
| 145 | H | 9-Et | —(CH₂)₄— | Me | 97 |
| 146 | H | 9-Et | —(CH₂)₃— | Me | 97 |
| 147 | H | 9-Et |  | Me | 46 |
| 148 | H | 9-Et | —(CH₂)₅— | Me | 88 |
| 149 | H | 9-Et | 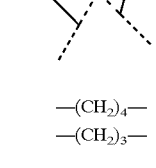 | Me | 5 |
| 150 | H | 9-Et | 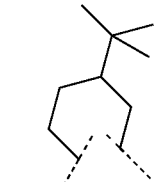 | Me | 32 |
| 151 | H | 9-Et | 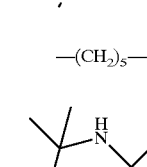 | Me | 31 |

TABLE 1a-continued

General structural formula

| Compound of formula | $R_1$ | $R_2$ | $R_6$ ring | $R_5$ | Yield [surfaces %] |
|---|---|---|---|---|---|
| 152 | H | 9-Et | N-isopropyl piperidinyl | Me | 85 |
| 153 | H | 9-Et | 4-methylcyclohexyl | Me | 87 |
| 154 | H | 9-Et | cyclohexyl-cyclopentyl | Me | 92 |
| 155 | H | 9-Et | 4-propylcyclohexyl | Me | 93 |
| 156 | H | 9-Et |  | Me | 27 |
| 157 | H | 9-Et | 4-tert-butylcyclohexyl | Me | 73 |
| 158 | H | 9-Et | N-ethyl piperidinyl | Me | 79 |

TABLE 1a-continued

General structural formula

| Compound of formula | $R_1$ | $R_2$ | $R_6$ ring | $R_5$ | Yield [surfaces %] |
|---|---|---|---|---|---|
| 159 | H | 9-Et | N-benzyl piperidinyl | Me | 13 |
| 160 | H | 9-Et | N-methyl piperidinyl | Me | 81 |
| 161 | H | 9-Et | —(CH$_2$)$_{10}$— | Me | 98 |
| 162 | H | 9-Et | —(CH$_2$)$_6$— | Me | 97 |
| 163 | H | 9-Et | tetramethyl cyclohexyl | Me | 55 |
| 164 | H | 7-MeO | —(CH$_2$)$_4$— | Me | 58 |
| 165 | H | 7-MeO | —(CH$_2$)$_3$— | Me | 54 |
| 166 | H | 7-MeO | tert-butyl cyclohexyl | Me | 93 |
| 167 | H | 7-MeO | —(CH$_2$)$_5$— | Me | 96 |
| 168 | H | 7-MeO | tetramethyl piperidinyl NH | Me | 7 |

TABLE 1a-continued

General structural formula

| Compound of formula | $R_1$ | $R_2$ | $R_6$ ring | $R_5$ | Yield [surfaces %] |
|---|---|---|---|---|---|
| 169 | H | 7-MeO | N-propyl piperidinyl | Me | 82 |
| 170 | H | 7-MeO | N-ethoxycarbonyl piperidinyl | Me | 36 |
| 171 | H | 7-MeO | N-isopropyl piperidinyl | Me | 71 |
| 172 | H | 7-MeO | 4-methylcyclohexyl | Me | 29 |
| 173 | H | 7-MeO | cyclopentyl-cyclohexyl | Me | 80 |
| 174 | H | 7-MeO | 4-propylcyclohexyl | Me | 68 |

TABLE 1a-continued

General structural formula

| Compound of formula | R₁ | R₂ | R₆ (ring) | R₅ | Yield [surfaces %] |
|---|---|---|---|---|---|
| 175 | H | 7-MeO | (t-butyl substituted cyclohexyl) | Me | 95 |
| 176 | H | 7-MeO | (N-ethyl piperidinyl) | Me | 79 |
| 177 | H | 7-MeO | (N-benzyl piperidinyl) | Me | 89 |
| 178 | H | 7-MeO | (N-methyl piperidinyl) | Me | 72 |
| 179 | H | 7-MeO | —(CH₂)₁₀— | Me | 73 |
| 180 | H | 7-MeO | —(CH₂)₆— | Me | 27 |
| 181 | H | 7-MeO | (tetramethyl cyclohexyl) | Me | 95 |

TABLE 1b

General structural formula

| Compound of formula | R₁ | R₂ | R₂' | ⟨R₆⟩ | R₄ | Yield [surfaces %] |
|---|---|---|---|---|---|---|
| 182 | —H | —H | —H | N-methyl azabicyclic | —H | 89 |
| 183 | —H | —H | —H | decalin | —H | 56 |
| 184 | —H | —H | —H | N-propyl piperidine | —H | 95 |
| 185 | —H | —H | —H | —(CH₂)₁₃— | —H | 82 |
| 186 | —H | 6-Me | —H | N-propyl piperidine | —H | 93 |
| 187 | —H | 6-OMe | —H | —(CH₂)₅— | —H | 90 |
| 188 | —H | 6-OMe | —H | —(CH₂)₁₀— | —H | 50 |
| 189 | —H | 6- OCH₂CH(OH)CH₂NH-iPr | —H | —(CH₂)₅— | —H | 85 |
| 190 | —H | 6- OCH₂CH(OH)CH₂NH-iPr | —H | N-propyl piperidine | —H | 40 |
| 191 | —H | 7-F | —H | —(CH₂)₅— | —H | 88 |
| 192 | —H | 7-F | —H | —(CH₂)₁₀— | —H | 93 |

TABLE 1b-continued

General structural formula

| Compound of formula | R₁ | R₂ | R₂' | R₆ (ring) | R₄ | Yield [surfaces %] |
|---|---|---|---|---|---|---|
| 193 | —H | 7-F | —H | N-propyl-piperidine | —H | 94 |
| 194 | —H | 7-Me | —H | —(CH₂)₅— | —H | 81 |
| 195 | —H | 7-Me | —H | —(CH₂)₁₀— | —H | 96 |
| 196 | —H | 8-Cl | —H | —(CH₂)₆— | —H | 87 |
| 197 | —H | 8-Cl | —H | —(CH₂)₁₀— | —H | 44 |
| 198 | —H | 8-Cl | —H | —(CH₂)₂— | —H | 97 |
| 199 | —H | 8-Cl | —H | N-propyl-piperidine | —H | 99 |
| 200 | —H | 6-COOMe | —H | —(CH₂)₂— | —H | 66 |
| 201 | —H | 6-COOMe | —H | N-propyl-piperidine | —H | 82 |
| 202 | —H | 8-Me | —H | —(CH₂)₅— | —H | 76 |
| 203 | —H | 8-Me | —H | N-propyl-piperidine | —H | 82 |
| 204 | —H | 8-F | —H | —(CH₂)₅— | —H | 76 |
| 205 | —H | 8-F | —H | —(CH₂)₁₀— | —H | 56 |
| 206 | —H | 8-F | —H | —(CH₂)₂— | —H | 75 |
| 207 | —H | 8-F | —H | N-propyl-piperidine | —H | 90 |
| 208 | —H | 9-F | —H | —(CH₂)₅— | —H | 93 |
| 209 | —H | 9-F | —H | —(CH₂)₁₀— | —H | 30 |
| 210 | —H | 9-F | —H | —(CH₂)₂— | —H | 89 |

TABLE 1b-continued

General structural formula

| Compound of formula | R$_1$ | R$_2$ | R$_2$' | (R$_6$ ring) | R$_4$ | Yield [surfaces %] |
|---|---|---|---|---|---|---|
| 211 | —H | 9-F | —H | N-propyl-piperidine | —H | 99 |
| 212 | —H | 8-CF$_3$ | —H | —(CH$_2$)$_5$— | —H | 42 |
| 213 | —H | 8-CF$_3$ | —H | —(CH$_2$)$_{10}$— | —H | 40 |
| 214 | —H | 8-CF$_3$ | —H | —(CH$_2$)$_2$— | —H | 61 |
| 215 | —H | 8-CF$_3$ | —H | N-propyl-piperidine | —H | 71 |
| 216 | —H | 7-F | 8-F | —(CH$_2$)$_5$— | —H | 68 |
| 217 | —H | 7-F | 8-F | —(CH$_2$)$_{10}$— | —H | 90 |
| 218 | —H | 7-F | 8-F | —(CH$_2$)$_2$— | —H | 87 |
| 219 | —H | 7-F | 8-F | N-propyl-piperidine | —H | 98 |
| 220 | —H | 9-Me | —H | —(CH$_2$)$_5$— | —H | 95 |
| 221 | —H | 9-Me | —H | —(CH$_2$)$_{10}$— | —H | 97 |
| 222 | —H | 9-Me | —H | N-propyl-piperidine | —H | 75 |
| 223 | —H | 6-Cl | —H | —(CH$_2$)$_2$— | —H | 95 |
| 224 | —H | 6-Cl | —H | N-propyl-piperidine | —H | 91 |
| 225 | —H | 6-F | —H | —(CH$_2$)$_2$— | —H | 94 |

TABLE 1b-continued

General structural formula

| Compound of formula | $R_1$ | $R_2$ | $R_2'$ | $R_6$ | $R_4$ | Yield [surfaces %] |
|---|---|---|---|---|---|---|
| 226 | —H | 6-F | —H | -CH2-CH2-CH2-N(piperidine) | —H | 97 |
| 227 | —H | 9-OMe | —H | —(CH$_2$)$_5$— | —H | 93 |
| 228 | —H | 9-OMe | —H | —(CH$_2$)$_{10}$— | —H | 90 |
| 229 | —H | 9-OMe | —H | -CH2-CH2-CH2-N(piperidine) | —H | 98 |
| 230 | —H | 8-OMe | —H | —(CH$_2$)$_5$— | —H | 84 |
| 231 | —H | 8-OMe | —H | -CH2-CH2-CH2-N(piperidine) | —H | 96 |
| 232 | —H | 7-COOMe | —H | —(CH$_2$)$_5$— | —H | 87 |
| 233 | —H | 7-COOMe | —H | —(CH$_2$)$_{10}$— | —H | 83 |
| 234 | —H | 7-COOMe | —H | —(CH$_2$)$_2$— | —H | 54 |
| 235 | —H | 7-COOMe | —H | -CH2-CH2-CH2-N(piperidine) | —H | 57 |
| 236 | —H | 7-OMe | 8-OMe | —(CH$_2$)$_5$— | —H | 99 |
| 237 | —H | 7-OMe | 8-OMe | —(CH$_2$)$_{10}$— | —H | 69 |
| 238 | —H | 7-OMe | 8-OMe | -CH2-CH2-CH2-N(piperidine) | —H | 58 |

The preparation of the tetrahydrocarbazoles according to the invention is carried out according to widely known methods in a 3-component reaction, as described in the publication by W. Noland et al., *J. Heterocycl. Chem.*, 1993, 30, 81–91.

For that purpose, mixtures of a (substituted) indole, ketone or aldehyde and a dienophile are reacted in a suitable solvent, e.g. 1-butanol, toluene, DMF, DMSO or Tetralin, using acid catalysts, e.g. hydrochloric acid, trifluoroacetic acid, toluenesulfonic acid, etc. The ketone or aldehyde component can also serve as solvent. The mixture is heated for several hours at a temperature of from 50° C. to 140° C. The resulting tetrahydrocarbazoles are filtered off and washed, or precipitated from the solvent with cold n-hexane and filtered off. Some of the substances are also obtained by concentrating the reaction mixture by evaporation.

The course of the reaction can be represented schematically as follows:

against bacteria of the skin flora, and also against yeasts and moulds. They are accordingly especially suitable for disinfection, deodorisation, and for the general and antimicrobial treatment of the skin and mucosa, and integumentary appendages (hair), especially for the disinfection of hands and wounds.

The compounds are accordingly suitable as antimicrobial active ingredients and as preservatives in personal care preparations, such as shampoos, bath additives, hair care products, liquid and solid soaps (based on synthetic surfactants and salts of saturated and/or unsaturated fatty acids), lotions and creams, deodorants, other aqueous or alcoholic solutions, e.g. cleansing solutions for the skin, moist wipes, oils or powders.

The invention accordingly relates also to a personal care preparation comprising at least one compound of formula (1) or (2) and cosmetically tolerable carriers or adjuvants.

The personal care preparation according to the invention contains from 0.01 to 15% by weight, preferably from 0.1 to

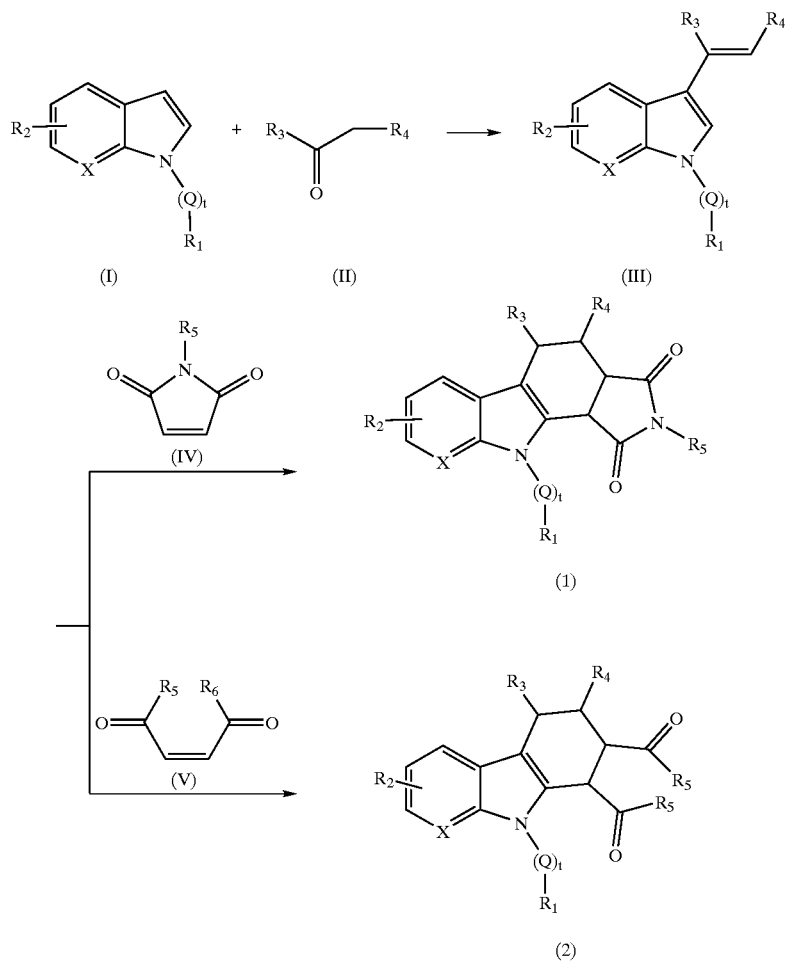

The tetrahydrocarbazoles obtained in that manner are generally obtained in the form of racemates and are mainly in the cis stereochemical form. Some compounds also form trans stereochemical isomers.

The invention relates also to the process for the preparation of those compounds.

The tetrahydrocarbazoles according to the invention exhibit pronounced antimicrobial activity, especially against pathogenic gram-positive and gram-negative bacteria and 10% by weight, based on the total weight of the composition, of a compound of formula (1) or (2) and cosmetically tolerable adjuvants.

Depending upon the form of the personal care preparation, it comprises, in addition to the compound of formula (1) or (2), further constituents, such as sequestering agents, colourings, perfume oils, thickening or solidifying agents (consistency regulators), emollients, UV-absorbers, skin protective agents, antioxidants, additives that improve the mechanical properties, such as dicarboxylic acids and/or aluminium, zinc, calcium or magnesium salts of $C_{14}$–$C_{22}$ fatty acids and, optionally, preservatives.

The personal care preparation according to the invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol.

Preferred mono- or poly-ols are ethanol, isopropanol, propylene glycol, hexylene glycol, glycerol and sorbitol.

Cosmetic formulations according to the invention are used in various fields. There come into consideration, for example, especially the following preparations:

- skin-care preparations, e.g. skin-washing and cleansing preparations in the form of tablet-form or liquid soaps, synthetic detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or compressed), rouge or cream make-up, eyecare preparations, e.g. eyeshadow preparations, mascara, eyeliner, eyecreams or eye-fix creams; lipcare preparations, e.g. lipsticks, lip gloss, lip contour pencils, nail-care preparations, such as nail varnish, nail varnish removers, nail hardeners or cuticle removers;
- intimate hygiene preparations, e.g. intimate washing lotions or intimate sprays;
- foot-care preparations, e.g. foot baths, foot powders, foot creams or foot balsams, special deodorants and anti-perspirants or callus-removing preparations;
- light-protective preparations, such as sun milks, lotions, creams, oils, sun-blocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de perfume, perfume de toilette, perfume), perfume oils or perfume creams;
- dental care, denture-care and mouth-care preparations, e.g. toothpastes, gel toothpastes, tooth powders, mouthwash concentrates, anti-plaque mouthwashes, denture cleaners or denture fixatives;
- cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hairsetting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:
0.01 to 5% by weight of a compound of formula (1) or (2),
0.3 to 1% by weight titanium dioxide,
1 to 10% by weight stearic acid,
ad 100% soap base, e.g. a sodium salt of tallow fatty acid or coconut fatty acid, or glycerol.

A shampoo has, for example, the following composition:
0.01 to 5% by weight of a compound of formula (1) or (2),
12.0% by weight sodium laureth-2-sulfate,
4.0% by weight cocamidopropylbetaine,
3.0% by weight NaCl and
water ad 100%.

A deodorant has, for example, the following composition:
0.01 to 5% by weight of a compound of formula (1) or (2),
60% by weight ethanol,
0.3% by weight perfume oil, and
water ad 100%.

The invention relates also to an oral composition comprising
0.01 to 15% by weight, based on the total weight of the composition, of a compound of formula (1) or (2), and orally tolerable adjuvants.

Example of an oral composition:
10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1) or (2) and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride or organic fluoride salts, e.g. amine fluorides, which are known under the trade name Olafluor.

The tetrahydrocarbazoles of formula (1) or (2) used according to the invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The tetrahydrocarbazoles according to the invention are suitable also for treating, especially imparting antimicrobial properties to or preserving, plastics, e.g. polyethylene, polypropylene, polyurethane, polyester, polyamide, polycarbonate, latex, etc. Fields of use therefore are, for example, floor coverings, plastics coatings, plastics container and packaging materials; kitchen and bathroom utensils (e.g. brushes, shower curtains, sponges, bathmats), latex, filter materials (air and water filters), plastics articles used in the field of medicine, e.g. dressing materials, syringes, catheters, etc., so-called "medical devices", gloves and mattresses.

Paper, for example papers used for hygiene purposes, may also be provided with antimicrobial properties using the tetrahydrocarbazoles according to the invention.

It is also possible for nonwovens, e.g. nappies/diapers, sanitary towels, panty liners, and cloths for hygiene and household uses, to be provided with antimicrobial properties in accordance with the invention.

The tetrahydrocarbazoles of formula (1) or (2) are also used in washing and cleaning formulations, e.g. in liquid or powder washing agents or softeners.

The tetrahydrocarbazoles of formula (1) or (2) can be used especially in household and general-purpose cleaners for cleaning and disinfecting hard surfaces.

A cleaning preparation has, for example, the following composition:

| | |
|---|---|
| 0.01 to 5% | of a compound of formula (1) or (2), |
| 3.0% | octyl alcohol 4EO, |
| 1.3% | fatty alcohol $C_8$–$C_{10}$ polyglucoside, |
| 3.0% | isopropanol, |
| ad 100% | water. |

In addition to preserving cosmetic and household products, the preservation of technical products, the provision of technical products with antimicrobial properties and use as a biocide in technical processes are also possible, for example in paper treatment, especially in paper treatment liquors, print thickeners of starch or of cellulose derivatives, surface coatings and paints.

The tetrahydrocarbazoles of formula (1) or (2) according to the invention are suitable also for the antimicrobial treatment of wood and for the antimicrobial treatment of leather, the preservation of leather and the provision of leather with antimicrobial properties.

The compounds according to the invention are also suitable for the protection of cosmetic products and household products from microbial damage.

The tetrahydrocarbazoles according to the invention are suitable also as medicaments for the treatment of bacterial infections for oral, intravenous, subcutaneous or parenteral administration of the active ingredient.

The invention accordingly relates also to a medicament comprising a compound of formula (1) or (2) and therapeutically tolerable adjuvants, for the treatment of bacterial infections.

The following Examples illustrate the invention.

General Procedure for the Preparation of the Tetrahydrocarbazoles According to the Invention:

The appropriate (substituted) indole (compound (I)) (1 mmol) is dissolved with (substituted) maleimide (compound (IV)) (1.2 mmol) and an aldehyde/ketone (compound (II)) (2 mmol) in 1-butanol (1 ml).

There is then added to the mixture aqueous hydrochloric acid (2N; 50 µl; 0.1 mmol) or, in the case of piperidones, concentrated hydrochloric acid (32%; 220 µl; 1.1 mmol). The mixture is then heated at 95° C. for 3 hours.

After cooling to 25° C., the resulting tetrahydrocarbazole (compound (1)) is precipitated with n-hexane (3 ml).

After filtration, the filtrate is cooled to 5° C. in order to obtain further crystals. The combined crystals are washed with n-hexane/ethyl acetate and dried in vacuo.

All the compounds, that is to say the compounds of formulae (9) to (181), are characterised by LC-MS (for yields, see Table 1). Some of the compounds are analysed by NMR spectroscopy. The compounds are obtained in the form of mixtures of isomers (racemates or exo/endo isomers).

PREPARATION EXAMPLES

Example 1

10-Bromo-3a,3b,4,5,6,7,8,8a,13,13b-decahydro-1H-cyclohepta[c]pyrrolo[3,4-a]carbazole-1,3(2H)-dione (compound of formula (32))

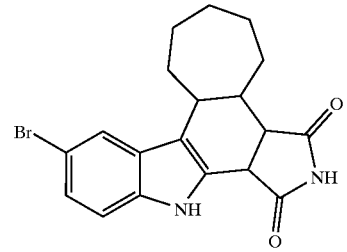

(32)

Yield: 72%

LC-MS: $[M+H]^+$=386 ($^{79}Br$)

NMR Data:

For reasons of clarity, the numbering used is not in accordance with IUPAC.

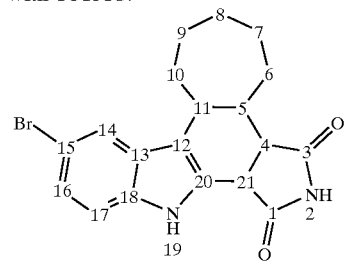

| Assignment | $d^1H$ [ppm] | $d^{13}C$ [ppm] |
|---|---|---|
| OC-1 | — | 176.5 |
| HN-1 | approx. 11 | — |
| OC-3 | — | 180.4 |
| HC-4 | 3.40 | 44.1 |
| HC-5 | 2.32 | 37.6 |
| $H_2$C-6 | 1.82 | 28.1 |
| | 1.58 | |
| $H_2$C-7 | 1.88 | 30.4 |
| | 1.28 | |
| $H_2$C-8 | 1.74 | 24.2 |
| | 1.41 | |
| $H_2$C-9 | 2.39 | 27.3 |
| | 1.81 | |
| $H_2$C-10 | 1.73 | 30.4 |
| HC-11 | 3.12 | 35.5 |
| C-12 | — | 114.1 |
| C-13 | — | 127.6 |
| HC-14 | 7.48 | 120.3 |

-continued

| Assignment | d¹H [ppm] | d¹³C [ppm] |
|---|---|---|
| C-15 | — | 111.0 |
| HC-16 | 7.16 | 123.6 |
| HC-17 | 7.31 | 113.5 |
| C18 | — | 135.7 |
| HN-19 | 11.11 | — |
| C-20 | — | 128.8 |
| HC-21 | 4.09 | 41.6 |

$^3J_{H-21,H-4} = 7.9$ Hz;
$^3J_{H-4,H-5} = 5.1$ Hz

Example 2

2,6-Dimethyl-3b,4,5,6,7,7a,12,12b-octahydrobenzo[c]pyrrolo[3,4 a]carbazole-1,3(2H,3aH)-dione (compound of formula (117))

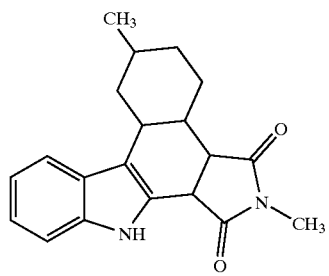

(117)

Yield: 79%

LC-MS: [M+H]⁺=322

NMR Data:

For reasons of clarity, the numbering used is not in accordance with IUPAC.

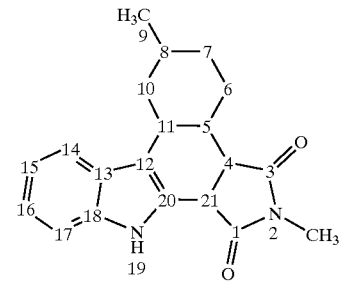

|  | Isomer A | | Isomer B | |
|---|---|---|---|---|
| Assignment | δ¹H [ppm] | δ¹³C [ppm] | δ¹H [ppm] | δ¹³C [ppm] |
| OC-1 | — | 175.6ᵃ | — | 175.9ᵇ |
| CH₃—N-2 | 2.81 | 24.4 | 2.72 | 24.2 |
| OC-3 | — | 178.6ᵃ | — | 177.7ᵇ |
| HC-4 | 3.44 | 43.9 | 3.45 | 44.3 |
| HC-5 | 2.35 | 33.8 | 1.58 | 40.8 |
| H₂C-6 | 1.99 | 26.1 | 2.33 | 29.2 |
|  | 1.73 |  | 1.83 |  |
| H₂C-7 | 1.85 | 30.2 | 1.80 | 35.1 |
|  | 1.51 |  | 0.96 |  |
| H₂C-8 | 1.67 | 30.8 | 1.58 | 31.7 |
| H₃C-9 | 0.79 | 21.8 | 0.96 | 22.5 |
| H₂C-10 | 1.86 | 37.7 | 2.84 | 40.0 |
|  | 0.96 |  | 0.91 |  |
| HC-11 | 3.02 | 33.6 | 2.56 | 34.9 |

-continued

|  | Isomer A | | Isomer B | |
|---|---|---|---|---|
| Assignment | δ¹H [ppm] | δ¹³C [ppm] | δ¹H [ppm] | δ¹³C [ppm] |
| C-12 | — | 113.9 | — | 113.4 |
| C-13 | — | 125.8 | — | 125.5 |
| HC-14 | 7.46 | 118.2ᶜ | 7.61 | 119.9ᶜ |
| HC-15 | 6.93 | 118.3 | 6.89 | 118.3 |
| HC-16 | 7.02ᵈ | 120.9 | 7.00ᵈ | 120.7 |
| HC-17 | 7.34 | 111.4 | 7.32 | 111.4 |
| C18 | — | 136.9 | — | 136.9 |
| HN-19 | 10.94 | — | 11.06 | — |
| C-20 | — | 126.6 | — | 127.6 |
| HC-21 | 4.21 | 43.8 | 4.23 | 42.3 |

Example 3

9-Bromo-6-methyl-3b,4,5,6,7,7a,12,12b-octahydrobenzo[c]pyrrolo[3,4-a]carbazole-1,3(2H,3aH)-dione (compound of formula (70))

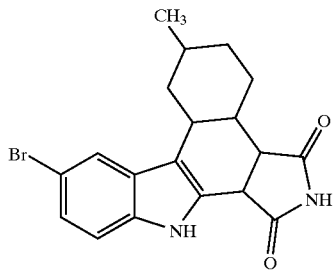

(70)

Yield: 71%

LC-MS: [M+H]⁺=386 (⁷⁹Br)

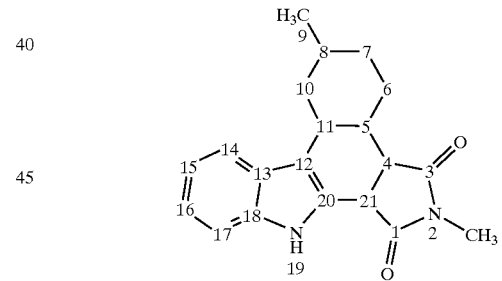

|  | Isomer A | | Isomer B | |
|---|---|---|---|---|
| Assignment | δ¹H [ppm] | δ¹³C [ppm] | δ¹H [ppm] | δ¹³C [ppm] |
| OC-1 | — | 175.6ᵃ | — | 175.9ᵇ |
| CH₃—N-2 | 2.81 | 24.4 | 2.72 | 24.2 |
| OC-3 | — | 178.6ᵃ | — | 177.7ᵇ |
| HC-4 | 3.44 | 43.9 | 3.45 | 44.3 |
| HC-5 | 2.35 | 33.8 | 1.58 | 40.8 |
| H₂C-6 | 1.99 | 26.1 | 2.33 | 29.2 |
|  | 1.73 |  | 1.83 |  |
| H₂C-7 | 1.85 | 30.2 | 1.80 | 35.1 |
|  | 1.51 |  | 0.96 |  |
| H₂C-8 | 1.67 | 30.8 | 1.58 | 31.7 |
| H₃C-9 | 0.79 | 21.8 | 0.96 | 22.5 |
| H₂C-10 | 1.86 | 37.7 | 2.84 | 40.0 |
|  | 0.96 |  | 0.91 |  |
| HC-11 | 3.02 | 33.6 | 2.56 | 34.9 |

-continued

| Assignment | Isomer A δ¹H [ppm] | Isomer A δ¹³C [ppm] | Isomer B δ¹H [ppm] | Isomer B δ¹³C [ppm] |
|---|---|---|---|---|
| C-12 | — | 113.9 | — | 113.4 |
| C-13 | — | 125.8 | — | 125.5 |
| HC-14 | 7.46 | 118.2ᶜ | 7.61 | 119.9ᶜ |
| HC-15 | 6.93 | 118.3 | 6.89 | 118.3 |
| HC-16 | 7.02ᵈ | 120.9 | 7.00ᵈ | 120.7 |
| HC-17 | 7.34 | 111.4 | 7.32 | 111.4 |
| C18 | — | 136.9 | — | 136.9 |
| HN-19 | 10.94 | — | 11.06 | — |
| C-20 | — | 126.6 | — | 127.6 |
| HC-21 | 4.21 | 43.8 | 4.23 | 42.3 |

Example 3

9-Bromo-6-methyl-3b,4,5,6,7,7a,12,12b-octahydrobenzo[c]pyrrolo[3,4-a]carbazole-1,3(2H,3aH)-dione (compound of formula (70))

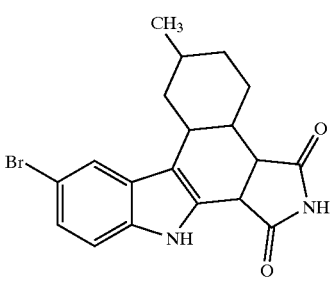

(70)

Yield: 71%

LC-MS: [M+H]⁺386 (⁷⁹Br)

NMR Data:

For reasons of clarity, the numbering used is not in accordance with IUPAC.

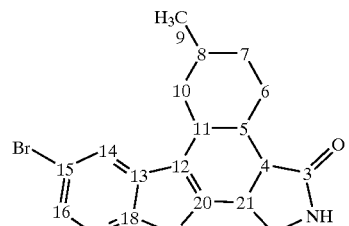

| Assignment | δ¹H [ppm] | δ¹³C [ppm] |
|---|---|---|
| OC-1 | — | 176.8 |
| HN-1 | 11.06 | — |
| OC-3 | — | 179.1 |
| HC-4 | 3.43 | ? |
| HC-5 | 1.50 | 40.6 |
| H₂C-6 | 2.26 / 1.75 | 29.1 |
| H₂C-7 | 1.76 / 0.94 | 35.1 |
| H₂C-8 | 1.56 | 31.7 |
| H₃C-9 | 0.96 | 22.6 |
| H₂C-10 | 2.75 / 0.85 | 39.7 |
| HC-11 | 2.57 | 34.7 |
| C-12 | — | 113.2 |
| C-13 | — | 127.3 |
| HC-14 | 7.76 | 121.8 |
| C-15 | — | 110.8 |
| HC-16 | 7.13 | 123.1 |
| HC-17 | 7.29 | 113.3 |
| C18 | — | 135.5 |
| HN-19 | 11.26 | — |
| C-20 | — | 129.8 |
| HC-21 | 4.14 | 42.9 |

$^3J_{H-21,H-4} = 7.9$ Hz
$^3J_{H-4,H-5} = 4.1$ Hz

The remaining compounds listed in Table 1 can be prepared in analogous manner.

4. Microbiological Test Results

Nutrient:

Casein/soybean flour peptone bouillon for the preparation of pre-cultures of the test bacteria and yeast.

Mycological slant agar for the pre-culture of moulds

Examples of Test Organisms:

Staphylococcus hominis DMS 20328
Escherichia coli NCTC 8196
Corynebacterium xerosis ATCC 373
Enterococcus hirae ATCC 10541
Micrococcus luteus ATCC 9341
Candida albicans ATCC 10259
Staphylococcus aureus (methicillin-resistant) NCTC 11940

Staphylococcus epidermidis ATCC 12228
P. ovale ATCC 14521
Actinomyces viscosus DSM 43329
Porphyromonas gingivalis DSM 20709
Selenomonas artemidis ATCC 43528
Streptococcus mutans ATCC 25175
Streptococcus sobrinus DSM 20742

-continued

| | |
|---|---|
| Staphylococcus aureus (methicillin-resistant) NCTC 12493 | Epidermophyton floccosum DSM 10709 |
| Staphylococcus aureus (penicillin-resistant) NCTC 10443 | Tr. mentagrophytes ATCC 9533 Trichophyton rubrum DSM 4167 |
| Staphylococcus aureus (rifampicin-resistant) NCTC 10703 | Trichoderma longibrachiatum DSM 768 |
| Propionibacterium acnes ATCC 25746 | Aspergillus niger ATCC 6175 |

Procedure:

The test substances are predissolved in dimethyl sulfoxide (DMSO) and tested in a dilution series of 1:2.

Bacteria and yeast are cultured overnight in CASO bouillon, the mould is cultured overnight on mycological slant agar, and washed off with 10 ml of 0.85% sodium chloride solution (+0.1% TritonX-100).

All the test organisms are adjusted to an organism count of $1-5\times10^6$ CFU/ml using 0.85% sodium chloride solution.

The test substances are pre-pipetted into microtitre plates in an amount of 8 µl per well.

Pre-diluted organism suspensions are diluted 1:100 in CASO bouillon (bacteria and yeast) or Sabouraud 2% glucose bouillon (mould) and are added in an amount of 192 µl per well to the test substances.

The test batches are incubated for 48 hours at 37° C. (bacteria and yeast) or for 5 days at 28° C. (mould).

After incubation, the growth is evaluated by reference to the turbidity of the test batches (optical density) at 620 nm in a microplate reader.

The minimum inhibitory concentration (MIC value) is the concentration of substance at which (compared with the growth of the control) an appreciable inhibition of growth ($\leq 20\%$ growth) of the test organisms is ascertained.

One microtitre plate is used for each test organism and substance concentration. All the substances are tested in duplicate.

The results are compiled in Table 2:

TABLE 2

Minimum inhibitory concentrations (MIC) in ppm of the compounds synthesised against *Staphylococcus hominis* DMS 20328 and *Escherichia coli*

| Compound of formula | MIC [ppm] S. hominis | MIC [ppm] E. coli |
|---|---|---|
| 9 | >36 | >36 |
| 10 | >48 | >48 |
| 11 | >120 | >120 |
| 12 | >120 | >120 |
| 13 | >120 | >120 |
| 14 | >120 | >120 |
| 15 | >120 | >120 |
| 16 | >120 | >120 |
| 17 | >120 | >120 |
| 18 | >120 | >120 |
| 19 | >120 | >120 |
| 20 | >120 | >120 |
| 21 | >120 | >120 |
| 22 | >120 | >120 |
| 23 | >64 | >64 |
| 24 | >120 | >120 |
| 25 | >120 | >120 |
| 26 | 15 | >120 |
| 27 | 60 | >120 |
| 28 | >120 | >120 |
| 29 | 15 | >120 |
| 30 | >120 | >120 |
| 31 | 15 | >120 |
| 32 | 3.75 | >120 |
| 33 | 30 | 60 |
| 34 | >120 | >120 |

TABLE 2-continued

Minimum inhibitory concentrations (MIC) in ppm of the compounds synthesised against *Staphylococcus hominis* DMS 20328 and *Escherichia coli*

| Compound of formula | MIC [ppm] S. hominis | MIC [ppm] E. coli |
|---|---|---|
| 35 | >120 | >120 |
| 36 | >120 | >120 |
| 37 | >120 | >120 |
| 38 | >120 | >120 |
| 39 | >120 | >120 |
| 40 | >120 | >120 |
| 41 | >120 | >120 |
| 42 | >120 | >120 |
| 43 | >120 | >120 |
| 44 | >120 | >120 |
| 45 | >120 | >120 |
| 46 | 120 | 120 |
| 47 | >120 | >120 |
| 48 | >120 | >120 |
| 49 | >120 | >120 |
| 50 | >120 | >120 |
| 51 | >120 | >120 |
| 52 | >120 | >120 |
| 53 | >120 | >120 |
| 54 | >120 | >120 |
| 55 | >120 | >120 |
| 56 | 30 | >120 |
| 57 | >120 | >120 |
| 58 | 30 | >120 |
| 59 | >120 | >120 |
| 60 | 120 | >120 |
| 61 | 3.75 | >120 |
| 62 | 15 | >120 |
| 63 | 7.5 | >120 |
| 64 | 120 | >120 |
| 65 | 120 | >120 |
| 66 | >120 | >120 |
| 67 | >120 | >120 |
| 68 | >120 | >120 |
| 69 | 120 | >120 |
| 70 | 15 | >120 |
| 71 | 60 | >120 |
| 72 | 120 | >120 |
| 73 | 60 | >120 |
| 74 | 60 | >120 |
| 75 | 30 | >120 |
| 76 | >120 | >120 |
| 77 | 15 | >120 |
| 78 | 60 | >120 |
| 79 | 120 | >120 |
| 80 | 120 | >120 |
| 81 | 60 | 120 |
| 82 | 30 | >120 |
| 83 | >120 | >120 |
| 84 | 120 | >120 |
| 85 | >120 | >120 |
| 86 | 120 | >120 |
| 87 | 15 | 120 |
| 88 | >120 | >120 |
| 89 | 7.5 | >120 |
| 90 | >120 | >120 |
| 91 | >120 | >120 |
| 92 | >120 | >120 |

TABLE 2-continued

Minimum inhibitory concentrations (MIC) in ppm of the compounds synthesised against *Staphylococcus hominis* DMS 20328 and *Escherichia coli*

| Compound of formula | MIC [ppm] S. hominis | MIC [ppm] E. coli |
|---|---|---|
| 93 | 60 | >120 |
| 94 | >120 | >120 |
| 95 | >120 | >120 |
| 96 | >120 | >120 |
| 97 | 120 | >120 |
| 98 | >120 | >120 |
| 99 | 120 | >120 |
| 100 | 120 | >120 |
| 101 | >120 | >120 |
| 102 | 60 | >120 |
| 103 | >120 | >120 |
| 104 | >120 | >120 |
| 105 | >120 | >120 |
| 106 | 3.75 | >120 |
| 107 | 120 | >120 |
| 108 | >120 | >120 |
| 109 | >120 | >120 |
| 110 | 120 | >120 |
| 111 | 60 | >120 |
| 112 | >120 | >120 |
| 113 | >120 | >120 |
| 114 | >120 | >120 |
| 115 | 60 | >120 |
| 116 | 120 | >120 |
| 117 | >120 | >120 |
| 118 | >120 | >120 |
| 119 | >120 | >120 |
| 120 | 30 | >120 |
| 121 | >120 | >120 |
| 122 | >120 | >120 |
| 123 | >120 | 120 |
| 124 | >120 | >120 |
| 125 | >120 | >120 |
| 126 | >120 | >120 |
| 127 | 60 | >120 |
| 128 | >120 | >120 |
| 129 | >120 | >120 |
| 130 | 15 | >120 |
| 131 | >120 | 120 |
| 132 | >120 | >120 |
| 133 | 120 | >120 |
| 134 | 120 | >120 |
| 135 | >120 | >120 |
| 136 | >120 | >120 |
| 137 | >120 | >120 |
| 138 | >120 | >120 |
| 139 | >120 | >120 |
| 140 | 120 | >120 |
| 141 | >120 | >120 |
| 142 | >120 | >120 |
| 143 | >120 | >120 |
| 144 | >120 | >120 |
| 145 | >120 | >120 |
| 146 | >120 | >120 |
| 147 | >120 | >120 |
| 148 | >120 | >120 |
| 149 | 120 | 120 |
| 150 | >120 | >120 |
| 151 | >120 | >120 |
| 152 | 120 | >120 |
| 153 | >120 | >120 |
| 154 | >120 | >120 |
| 155 | >120 | >120 |
| 156 | >120 | >120 |
| 157 | >120 | >120 |
| 158 | >120 | >120 |
| 159 | 7.5 | 120 |
| 160 | 120 | 120 |
| 161 | >120 | >120 |
| 162 | 120 | >120 |
| 163 | >120 | >120 |
| 164 | >120 | >120 |
| 165 | 120 | >120 |
| 166 | >120 | >120 |
| 167 | >120 | >120 |
| 168 | >120 | >120 |
| 169 | >120 | >120 |
| 170 | >120 | >120 |
| 171 | >120 | >120 |
| 172 | >120 | >120 |
| 173 | >120 | >120 |
| 174 | 30 | >120 |
| 175 | >120 | >120 |
| 176 | >120 | >120 |
| 177 | 120 | 120 |
| 178 | >120 | >120 |
| 179 | >120 | >120 |
| 180 | >120 | >120 |
| 181 | >120 | >120 |

TABLE 3

Further minimum inhibitory concentrations (MIC) in ppm of selected compounds (MIC values in ppm)

| Microorganism | Compound of formula | | | | | |
|---|---|---|---|---|---|---|
| | 61 | 63 | 70 | 87 | 89 | 106 |
| *Staphylococcus hominis* DSM 20328 | 3.75 | 7.5 | 15 | 15 | 7.5 | 3.75 |
| *Staphylococcus epidermidis* ATCC 12228 | ≦3.75 | ≦3.75 | 15 | 15 | ≦3.75 | ≦3.75 |
| *Corynebacterium xerosis* ATCC 373 | ≦3.75 | ≦3.75 | 7.5 | 7.5 | ≦3.75 | ≦3.75 |

TABLE 3-continued

Further minimum inhibitory concentrations (MIC) in ppm of selected compounds
(MIC values in ppm)

| Microorganism | Compound of formula | | | | | |
|---|---|---|---|---|---|---|
| | 61 | 63 | 70 | 87 | 89 | 106 |
| Enterococcus hirae ATCC 10541 | 7.5 | 7.5 | 60 | 30 | >120 | >120 |
| Micrococcus luteus ATCC 9341 | ≦3.75 | ≦3.75 | 15 | 15 | ≦3.75 | ≦3.75 |
| Candida albicans ATCC 10259 | >120 | >120 | >120 | >120 | >120 | >120 |

TABLE 4

Minimum inhibitory concentrations (MIC) in ppm of compound
(32) against methicillin, penicillin-resistant Staphylococci and
other microorganisms
>(MIC values in ppm)
Compound of formula (32)

| Microorganism | | Microorganism | |
|---|---|---|---|
| Staphylococus aureus ATCC 9144 | 5.0 ppm | P. ovale ATCC 14521 | >10 ppm |
| Staphylococcus hominis DSM 20328 | 5.0 ppm | Actinomyces viscosus DSM 43329 | 6.25 ppm |
| Staphylococcus aureus (methicillin-resistant) NCTC 11940 | 5.0 ppm | Porphyromonas gingivalis DSM 20709 | 3.125 ppm |
| Staphylococcus aureus (methicillin-resistant) NCTC 12493 | 5.0 ppm | Selenomonas artemidis ATCC 43528 | 50.0 ppm |
| Staphylococcus aureus (penicillin-resistant) NCTC 10443 | 5.0 ppm | Streptococcus mutans ATCC 25175 | 5.0 ppm |
| Staphylococcus aureus (rifampicin-resistant) NCTC 10703 | 5.0 ppm | Streptococcus sobrinus DSM 20742 | 6.25 ppm |
| S. epidermidis ATCC 12228 | 10 ppm | Candida albicans ATCC 10259 | >10 ppm |
| Corynebacterium xerosis ATCC 373 | 5.0 ppm | Epidermophyton floccosum DSM 10709 | 5.0 ppm |
| Micrococcus luteus ATCC 9341 | 5.0 ppm | Tr. mentagrophytes ATCC 9533 | 10 ppm |
| Enterococcus hirae ATCC 10541 | >10 ppm | Trichophyton rubrum DSM 4167 | 10 ppm |
| Propionibacterium acnes ATCC 25746 | 6.25 ppm | Trichoderma longibrachiatum DSM 768 | >10 ppm |
| | | Aspergillus niger ATCC 6175 | >10 ppm |

TABLE 5

Minimum inhibitory concentrations (MIC) in ppm of
selected synthesised compounds against
selected test organisms

| Compound of formula | MIC [ppm] S. hominis | MIC [ppm] E. coil | MIC [ppm] P. aeruginosa | MIC [ppm] A. niger |
|---|---|---|---|---|
| 182 | >120 | >120 | >120 | >120 |
| 183 | 15 | >120 | >120 | >120 |
| 184 | >120 | >120 | >120 | >120 |
| 185 | >120 | >120 | >120 | >120 |
| 186 | >120 | >120 | 120 | >120 |
| 187 | 30 | >120 | 60 | >120 |
| 188 | 15 | >120 | >120 | >120 |
| 189 | 15 | 120 | >120 | >120 |
| 190 | >120 | >120 | >120 | >120 |
| 191 | 7.5 | >120 | >120 | 120 |
| 192 | 7.5 | >120 | >120 | >120 |
| 193 | >120 | 60 | >120 | >120 |
| 194 | 7.5 | >120 | >120 | >120 |
| 195 | 15 | >120 | >120 | >120 |
| 196 | 7.5 | >120 | >120 | >120 |
| 197 | >120 | >120 | 120 | >120 |
| 198 | >120 | >120 | >120 | >120 |
| 199 | 120 | >120 | >120 | >120 |
| 200 | >120 | >120 | 120 | >120 |
| 201 | >120 | >120 | 60 | >120 |
| 202 | 60 | >120 | 120 | >120 |
| 203 | >120 | >120 | >120 | >120 |
| 204 | 15 | 120 | 60 | >120 |
| 205 | 7.5 | >120 | 120 | >120 |
| 206 | 7.5 | >120 | 60 | >120 |
| 207 | >120 | >120 | 120 | >120 |
| 208 | 15 | >120 | >120 | >120 |
| 209 | 30 | >120 | 120 | >120 |
| 210 | 120 | >120 | 120 | >120 |
| 211 | >120 | 120 | 120 | >120 |
| 212 | 120 | >120 | >120 | >120 |
| 213 | >120 | >120 | >120 | >120 |

TABLE 5-continued

Minimum inhibitory concentrations (MIC) in ppm of selected synthesised compounds against selected test organisms

| Compound of formula | MIC [ppm] S. hominis | MIC [ppm] E. coli | MIC [ppm] P. aeruginosa | MIC [ppm] A. niger |
|---|---|---|---|---|
| 214 | 15 | 120 | 120 | 120 |
| 215 | 30 | 60 | 120 | >120 |
| 216 | 15 | 120 | 120 | 120 |
| 217 | <3.75 | >120 | >120 | >120 |
| 218 | 15 | >120 | 120 | >120 |
| 219 | >120 | >120 | >120 | >120 |
| 220 | 15 | >120 | >120 | >120 |
| 221 | 15 | >120 | 60 | >120 |
| 222 | 120 | 120 | >120 | >120 |
| 223 | >120 | >120 | 60 | >120 |
| 224 | >120 | >120 | 120 | >120 |
| 225 | 120 | >120 | 120 | >120 |
| 226 | 120 | 120 | >120 | >120 |
| 227 | >120 | >120 | >120 | >120 |
| 228 | 15 | >120 | >120 | >120 |
| 229 | >120 | >120 | >120 | >120 |
| 230 | 120 | >120 | 120 | >120 |
| 231 | 120 | >120 | 120 | >120 |
| 232 | >120 | >120 | >120 | >120 |
| 233 | 15 | >120 | 120 | >120 |
| 234 | >120 | >120 | 120 | >120 |
| 235 | 120 | >120 | >120 | >120 |
| 236 | >120 | >120 | 120 | >120 |
| 237 | >120 | >120 | 120 | >120 |
| 238 | >120 | >120 | >120 | >120 |
| 239 | 120 | 120 | >120 | >120 |

What is claimed is:

1. A compound of formula

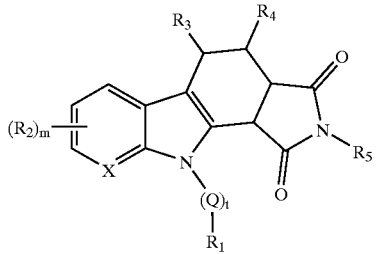

(1)

wherein $R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxycarbonyl, cyano, trifluoromethyl, pentafluoroethyl, amino, N,N-mono or di-$C_1$–$C_{20}$alkylamino or by nitro, $R_2$ is hydrogen; hydroxy; $C_1$–$C_{20}$alkyl; $C_3$–$C_{12}$cycloalkyl; $C_1$–$C_{20}$hydroxyalkyl; $C_1$–$C_{20}$hydroxy-alkoxy; $C_1$–$C_{20}$aminoalkyl; N—$C_1$–$C_{20}$monoalkylamino-$C_1$–$C_{20}$alkyl; N—$C_1$–$C_{20}$monoalkyl-aminohydroxy-$C_1$–$C_{20}$alkoxy; N,N—$C_1$–$C_{20}$dialkylamino-$C_1$–$C_{20}$alkyl; N,N—$C_1$–$C_{20}$dialkylaminohydroxy-$C_1$–$C_{20}$alkoxy; carboxy; carboxy-$C_1$–$C_{20}$alkyl ester; $C_1$–$C_{20}$haloalkyl; $C_1$–$C_{20}$-haloalkoxy; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$-alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_3$ and $R_4$ together denote a —(CH$_2$)$_{10}$— radical; a $C_2$–$C_{20}$alkenylene radical; a $C_4$–$C_{20}$-alkynylene radical; or a $C_3$–$C_{20}$alkylene radical interrupted by —N(R$_6$)—, it being possible for such bivalent radicals to be further substituted by one or more $C_1$–$C_{20}$alkyl, $C_3$–$C_{12}$-cycloalkyl, $C_2$–$C_{20}$alkenyl, $C_4$–$C_{12}$cycloalkenyl, $C_3$–$C_{20}$alkynyl, CC$_{12}$cycloalkynyl, $C_1$–$C_7$alkoxycarbonyl, or phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$-alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro; or $R_3$ and $R_4$ together denote a bicyclo[x.y.z.]$C_4$–$C_{20}$alkylene or bicyclo[x.y.z.]$C_4$–$C_{20}$alkylene interrupted by —N(R$_6$)—, wherein x and y are each independently of the other from 1 to 10 and z is from 0 to 10;

$R_5$ is hydrogen; hydroxy; $C_1$–$C_{20}$alkyl; $C_1$–$C_{20}$alkoxy; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$C$_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

Q is —SO$_2$—; —O—; or —(CO)—;

X is —CH—; or —N—;

m is from 1 to 3; and t is 0 or 1, or a compound of formula (2)

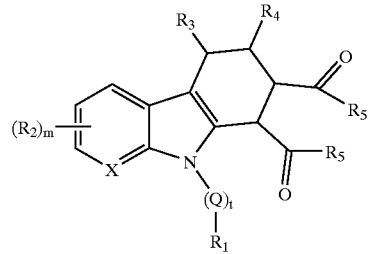

(2)

wherein $R_1$, $R_2$, $R_6$, X, Q, t and m are as defined for the compound of formula (1);

$R_3$ and $R_4$ are each independently of the other hydrogen; or $C_1$–$C_{20}$alkyl; or $R_3$ and $R_4$ together denote a $C_2$–$C_{20}$alkylene radical; a $C_2$–$C_{20}$alkenylene radical; a $C_4$–$C_{20}$-alkynylene radical; or a $C_3$–$C_{20}$alkylene radical interrupted by —N(R$_6$)—, it being possible for such bivalent radicals to be further substituted by one or more $C_1$–$C_{20}$alkyl, $C_3$–$C_{12}$-cycloalkyl, $C_2$–$C_{20}$alkenyl, $C_4$–$C_{12}$cycloalkenyl, $C_3$–$C_{20}$alkynyl, $C_4$–$C_{12}$cycloalkynyl, $C_1$–$C_7$-alkoxycarbonyl, or phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$-alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro; or $R_3$ and $R_4$ together denote a bicyclo[x.y.z.]$C_4$–$C_{20}$alkylene; or bicyclo[x.y.z.]$C_4$–$C_{20}$alkylene interrupted by —N($R_6$)—, wherein x and y are each independently of the other from 1 to 10 and z is from 0 to 10;

$R_5$ is hydrogen; $C_1$–$C_{20}$alkyl; phenyl or phenyl-$C_1$–$C_5$alkyl.

2. A compound of formula (1) according to claim 1, wherein $R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxycarbonyl, cyano, trifluoromethyl, pentafluoroethyl, amino, N,N-mono- or di-$C_1$–$C_{20}$alkylamino or by nitro, $R_2$ is hydrogen; hydroxy; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_3$ and $R_4$ together denote a —$(CH_2)_{10}$— radical; a $C_2$–$C_{20}$alkenylene radical; a $C_4$–$C_{20}$alkynylene radical; or a $C_3$–$C_{20}$alkylene radical interrupted by —N($R_6$)—, it being possible for such bivalent radicals to be further substituted by one or more $C_1$–$C_{20}$alkyl, $C_3$–$C_{12}$cycloalkyl, $C_2$–$C_{20}$-alkenyl, $C_4$–$C_{12}$cycloalkenyl, $C_3$–$C_{20}$alkynyl, $C_4$–$C_{12}$cycloalkynyl, $C_1$–$C_7$alkoxycarbonyl, or phenyl or phenyl-$C_1$–$C_5$alkyl each unsubstituted or substituted by $C_1$–$C_5$alkyl, $C_3$–$C_{12}$-cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

$R_5$ is hydrogen; hydroxy; $C_1$–$C_{20}$alkyl; $C_1$–$C_{20}$alkoxy; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cyclo-alkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cyclo-alkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

Q is —$SO_2$—; —O—; or —(CO)—;
X is —CH—; or —N—;
m is from 1 to 3; and
t is 0 or 1, or a compound of formula (2) according to claim 1, wherein
$R_1$, $R_2$, $R_2$, X, Q, t and m are as defined above for the compound of formula (1) and $R_3$ and $R_4$ are each independently of the other hydrogen; or $C_1$–$C_{20}$alkyl; or $R_3$ and $R_4$ denote a $C_2$–$C_{20}$alkylene radical; a $C_2$–$C_{20}$alkenylene radical; a $C_4$–$C_{20}$alkynylene radical; or a $C_3$–$C_{20}$alkylene radical interrupted by —N($R_6$)—, it being possible for such bivalent radicals to be further substituted by one or more $C_1$–$C_{20}$alkyl, $C_3$–$C_{12}$cycloalkyl, $C_2$–$C_{20}$-alkenyl, $C_4$–$C_{12}$cycloalkenyl, $C_3$–$C_{20}$alkynyl, $C_4$–$C_{12}$cycloalkynyl, $C_1$–$C_7$alkoxycarbonyl, or phenyl or phenyl-$C_1$–$C_5$alkyl each unsubstituted or substituted by $C_1$–$C_5$alkyl, $C_3$–$C_{12}$-cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

$R_5$ is hydrogen; $C_1$–$C_{20}$alkyl; phenyl or phenyl-$C_1$–$C_5$alkyl.

3. A compound according to claim 1, wherein
$R_1$ is hydrogen; $C_1$–$C_{20}$alkyl; phenyl or phenyl-$C_1$–$C_5$alkyl.

4. A compound according to claim 1, wherein
$R_1$ is hydrogen; or $C_1$–$C_5$alkyl.

5. A compound according to claim 1, wherein
$R_2$ is hydrogen; $C_1$–$C_{20}$alkyl; $C_1$–$C_{20}$alkoxy; or halogen.

6. A compound according claim 1, wherein
$R_2$ is hydrogen; $C_1$–$C_5$alkyl; $C_1$–$C_5$alkoxy; or halogen.

7. A compound according to claim 1 that corresponds to formula (3)

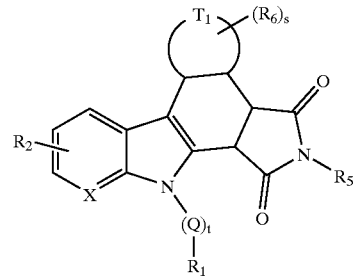

wherein $R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxycarbonyl, cyano, trifluoromethyl, pentafluoroethyl, amino, N-mono- or N,N-di-$C_1$–$C_{20}$alkylamino or by nitro, $R_2$ is hydrogen; hydroxy; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_5$ is hydrogen; hydroxy; $C_1$–$C_{20}$alkyl; $C_1$–$C_{20}$alkoxy; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cyclo-alkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- or N,N-di-$C_1$–$C_{20}$alkylamino or by nitro;

R₆ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cyclo-alkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N-mono- N,N-or di-$C_1$–$C_{20}$alkylamino or by nitro;

Q is —SO₂—; —O—; or —(CO)—;

T₁ is $C_2$–$C_{20}$alkenylene; $C_4$–$C_{20}$alkynylene; or $C_3$–$C_{20}$alkylene interrupted by

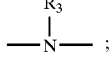

X is —CH—; or —N—;
s is from 1 to 4; and
t is 0 or 1, or
a compound according to claim 1 that corresponds to formula (4)

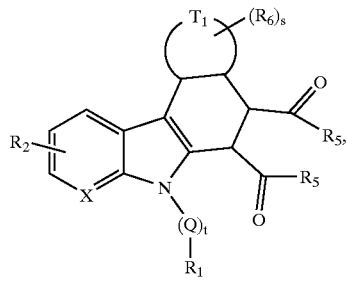

wherein

R₁, R₂, R₆, X, Q, t and s have the same definitions as above for the compound of formula (3); and T₁ is $C_2$–$C_{20}$alkylene; $C_2$–$C_{20}$alkenylene; $C_4$–$C_{20}$alkynylene; or $C_3$–$C_{20}$alkylene interrupted by

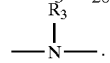

8. A compound of formula (4) according to claim 7, wherein
T₁ is a —(CH₂)₁₀— radical; and
R₆ is hydrogen; or $C_1$–$C_5$alkyl.

9. A compound according to claim 1, wherein
R₅ is hydrogen; $C_1$–$C_{20}$alkyl; phenyl or phenyl-$C_1$–$C_5$alkyl.

10. A compound according to claim 1, wherein
R₅ is hydrogen; $C_1$–$C_5$alkyl; or phenyl.

11. A compound of formula (5)

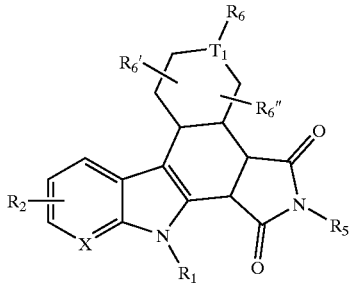

wherein

R₆' and R₆'' are each independently of the other hydrogen; $C_1$–$C_{20}$alkyl; $C_1$–$C_7$alkoxy-carbonyl; phenyl or phenyl-$C_1$–$C_5$alkyl each unsubstituted or substituted by $C_1$–$C_5$alkyl, $C_1$–$C_7$alkoxycarbonyl, N-mono- or N,N-di-$C_1$–$C_{20}$alkylamino or by nitro;

T₁ is —(CH₂)₇— or

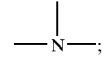

and
R₁, R₂, R₅, R₆ and X are as defined in claim 7, or a compound of formula (6)

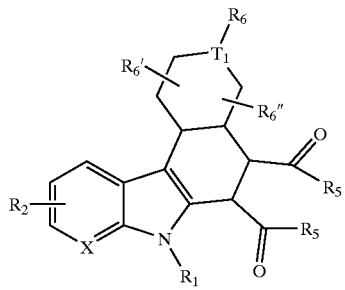

wherein

R₆' and R₆'' are each independently of the other hydrogen; $C_1$–$C_{20}$alkyl; $C_1$–$C_7$alkoxy-carbonyl; phenyl or phenyl-$C_1$–$C_5$alkyl each unsubstituted or substituted by $C_1$–$C_5$alkyl, $C_1$–$C_7$alkoxycarbonyl, N-mono- or N,N-di-$C_1$–$C_{20}$alkylamino or by nitro;

T₁ is

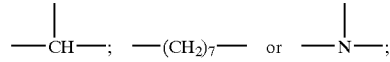

and
R₁, R₂, R₅, R₆ and X are as defined in claim 7.

12. A compound according to claim 11, wherein
R₆', R₆'' and R₆ are each independently of the others hydrogen; $C_1$–$C_{20}$alkyl; $C_1$–$C_7$-alkoxycarbonyl; phenyl; or phenyl-$C_1$–$C_5$alkyl.

13. A compound according to claim 12, wherein
R₆', R₆'' and R₆ are each independently of the others hydrogen; $C_1$–$C_5$alkyl; $C_1$–$C_7$alkoxycarbonyl; phenyl or benzyl.

14. A compound according to claim 11 that corresponds to formula (7)

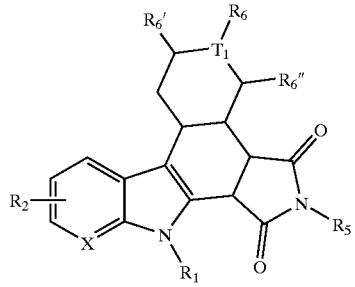

wherein

R₁ is hydrogen; or $C_1$–$C_5$alkyl;
R₂ is hydrogen; $C_1$–$C_4$alkyl; Cl or Br;
R₅ is hydrogen; $C_1$–$C_5$alkyl; or phenyl
R₆' and R₆'' are each independently of the other hydrogen; $C_1$–$C_5$alkyl; or $C_1$–$C_7$alkoxy-carbonyl;
R₆ is hydrogen, $C_1$–$C_5$alkyl; $C_1$–$C_7$alkylcarbonyl; or phenyl-$C_1$–$C_5$alkyl;

$T_1$ is

and

X is —CH—, or a compound according to claim 11 that corresponds to formula (8)

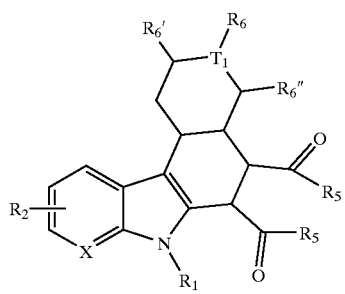

wherein $R_1$ is hydrogen; or $C_1$–$C_5$alkyl;

$R_2$ is hydrogen; $C_1$–$C_4$alkyl; Cl or Br;

$R_5$ is hydrogen; $C_1$–$C_5$alkyl; or phenyl $R_6{}'$ and $R_6{}''$ are each independently of the other hydrogen; $C_1$–$C_5$alkyl; or $C_1$–$C_7$alkoxy-carbonyl;

$R_6$ is hydrogen, $C_1$–$C_5$alkyl; $C_1$–$C_7$alkylcarbonyl; or phenyl-$C_1$–$C_5$alkyl;

$T_1$ is

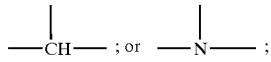

and

X is —CH—.

15. A personal care method for antimicrobial treatment, deodorisation and disinfection of skin, mucosa or hair, which comprises contacting the skin, mucosa or hair with an effective amount of a compound of formula (1) or (2)

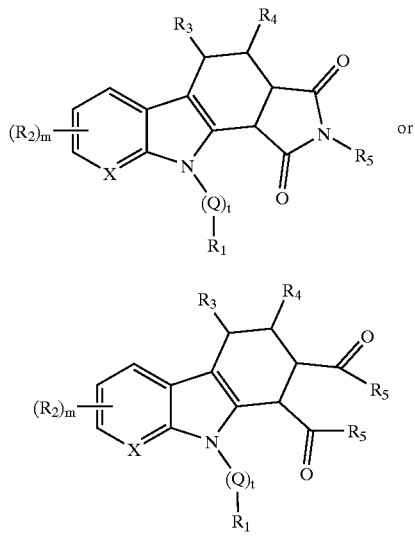

wherein $R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxycarbonyl, cyano, trifluoromethyl, pentafluoroethyl, amino, N,N-mono- or di-$C_1$–$C_{20}$alkylamino or by nitro, $R_2$ is hydrogen; hydroxy; $C_1$–$C_{20}$alkyl; $C_3$–$C_{12}$cycloalkyl; $C_1$–$C_{20}$hydroxyalkyl; $C_1$–$C_{20}$-hydroxy-alkoxy; $C_1$–$C_{20}$aminoalkyl; N—$C_1$–$C_{20}$monoalkylamino-$C_1$–$C_{20}$alkyl; N—$C_1$–$C_{20}$-monoalkyl-aminohydroxy-$C_1$–$C_{20}$alkoxy; N,N—$C_1$–$C_{20}$dialkylamino-$C_1$–$C_{20}$alkyl; N,N—$C_1$–$C_{20}$dialkyl-aminohydroxy-$C_1$–$C_{20}$alkoxy; carboxy; carboxy-$C_1$–$C_{20}$alkyl ester; $C_1$–$C_{20}$haloalkyl; $C_1$–$C_{20}$haloalkoxy; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_3$ is hydrogen and $R_4$ is $C_1$–$C_{20}$alkyl; or $R_4$ is hydrogen and $R_3$ is $C_1$–$C_{20}$alkyl; or $R_3$ and $R_4$ together denote a $C_2$–$C_{20}$alkylene radical; a $C_2$–$C_{20}$alkenylene radical; a $C_4$–$C_{20}$-alkynylene radical; or a $C_3$–$C_{20}$alkylene radical interrupted by —N($R_6$)—, it being possible for such bivalent radicals to be further substituted by one or more $C_1$- $C_1$–$C_{20}$alkyl, $C_3$–$C_{12}$-cycloalkyl, $C_2$–$C_{20}$alkenyl, $C_4$–$C_{12}$cycloalkenyl, $C_3$–$C_{20}$alkynyl, $C_4$–$C_{12}$cycloalkynyl, $C_1$–$C_7$-alkoxycarbonyl, or phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$-alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro; or $R_3$ and $R_4$ together denote a bicyclo[x.y.z]$C_4$–$C_{20}$alkylene; or bicyclo[x.y.z.]$C_4$–$C_{20}$alkylene interrupted by —N($R_6$)—, wherein x, y and z are each independently of the others from 0 to 10;

$R_5$ is hydrogen; hydroxy: $C_1$–$C_{20}$alkyl; $C_1$–$C_{20}$alkoxy; $C_3$–$C_{12}$cycloalkyl; $C_3$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or N,N-di-$C_1$–$C_{20}$alkylamino or by nitro;

Q is —$SO_2$—; —O—; or —(CO)—;

X is —CH—; or —N—;

m is from 1 to 3; and t is 0 or 1.

16. A method according to claim 15, wherein the compound of formula (1) or (2) is used for disinfection and deodorisation.

17. A method for preserving textile fibre materials, which comprises contacting the textile fibre materials with an effective amount of a compound of formula (1) or (2) according to claim 15.

18. A method of preparing and preserving washing and cleaning formulations, which comprises incorporating therein an effective amount of a compound of formula (1) or (2) according to claim 15.

19. A method of imparting antimicrobial properties to and preserving plastics, paper, nonwovens, wood or leather, which comprises contacting the plastics, paper, nonwovens, wood or leather with an effective amount of a compound of formula (1) or (2) according to claim 15.

20. A method of imparting antimicrobial properties to and preserving technical products selected from the group consisting of print thickeners of starch or of cellulose derivatives, surface coatings and paints, which comprises contacting said technical products with an effective amount of a compound of formula (1) or (2) according to claim 15.

21. A method for biocidal treatment of paper, which comprises contacting said paper with a biocidally effective amount of a compound of formula (1) or (2) according to claim 15.

22. An antimicrobial personal care preparation comprising from 0.01 to 15% by weight, based on the total weight of the composition, of a compound of formula (1) or (2)

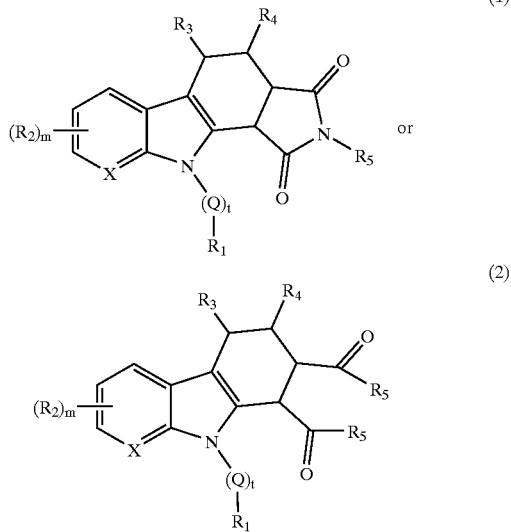

wherein
$R_1$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkylcarbonyl, $C_1$–$C_7$alkoxycarbonyl, $C_3$–$C_{12}$cycloalkylcarbonyl, $C_3$–$C_{12}$-cycloalkoxycarbonyl, cyano, trifluoromethyl, pentafluoroethyl, amino, N,N-mono- or di-$C_1$–$C_{20}$alkylamino or by nitro, $R_2$ is hydrogen; hydroxy; $C_1$–$C_{20}$alkyl; $C_3$–$C_{12}$cycloalkyl; $C_1$–$C_{20}$hydroxyalkyl; $C_1$–$C_{20}$hydroxy-alkoxy; $C_1$–$C_{20}$aminoalkyl; N—$C_1$–$C_{20}$monoalkylamino-$C_1$–$C_{20}$alkyl; N—$C_1$–$C_{20}$-monoalkyl-aminohydroxy-$C_1$–$C_{20}$alkoxy; N,N—$C_1$–$C_{20}$dialkylamino-$C_1$–$C_{20}$alkyl; N,N—$C_1$–$C_{20}$dialkyl-aminohydroxy-$C_1$–$C_{20}$alkoxy; carboxy; carboxy-$C_1$–$C_{20}$alkyl ester; $C_1$–$C_{20}$haloalkyl; $C_1$–$C_{20}$-haloalkoxy; $C_2$–$C_{20}$alkenyl; $C_4$–$C_{12}$cycloalkenyl; $C_3$–$C_{20}$alkynyl; $C_4$–$C_{12}$cycloalkynyl; $C_1$–$C_{20}$-alkoxy; $C_2$–$C_{20}$alkenyloxy; $C_2$–$C_{20}$alkynyloxy; halogen; cyano; $C_1$–$C_7$alkylcarbonyl; nitro; trifluoromethyl; or pentafluoroethyl;

$R_3$ is hydrogen and $R_4$ is $C_1$–$C_{20}$alkyl; or $R_4$ is hydrogen and $R_3$ is $C_1$–$C_{20}$alkyl; or $R_3$ and $R_4$ together denote a $C_2$–$C_{20}$alkylene radical; a $C_2$–$C_{20}$alkenylene radical; a $C_4$–$C_{20}$-alkynylene radical; or a $C_3$–$C_{20}$alkylene radical interrupted by —N($R_6$)—, it being possible for such bivalent radicals to be further substituted by one or more $C_1$- $C_1$–$C_{20}$alkyl, $C_3$–$C_{12}$-cycloalkyl, $C_2$–$C_{20}$alkenyl, $C_4$–$C_{12}$cycloalkenyl, $C_3$–$C_{20}$alkynyl, $C_4$–$C_{12}$cycloalkynyl, $C_1$–$C_7$-alkoxycarbonyl, or phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$-alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro; or $R_3$ and $R_4$ together denote a bicyclo[x.y.z]$C_4$–$C_{20}$alkylene; or bicyclo[x.y.z.]$C_4$–$C_{20}$alkylene interrupted by —N($R_6$)—, wherein x, y and z are each independently of the others from 0 to 10;

$R_5$ is hydrogen; hydroxy: $C_1$–$C_{20}$alkyl; $C_1$–$C_{20}$alkoxy; $C_3$–$C_{12}$cycloalkyl; $C_3$–$C_{20}$alkenyl; $C_4$–$C_{12}$cycloalkenyl; $C_3$–$C_{20}$alkynyl; $C_4$–$C_{12}$cycloalkynyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$$C_7$alkoxycarbonyl, $C_3$–$C_{12}$cycloalkoxycarbonyl, cyano, trifluoromethyl, pentafluoroethyl, amino, N,N-mono- or di-$C_1$–$C_{20}$alkylamino or by nitro;

$R_6$ is hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$-alkynyl; $C_4$–$C_{12}$cycloalkynyl; $C_1$–$C_7$alkoxycarbonyl; phenyl or phenyl-$C_1$–$C_5$alkyl each unsubstituted or substituted by $C_1$–$C_5$alkyl, $C_3$–$C_{12}$cycloalkyl, $C_1$–$C_5$alkoxy, $C_3$–$C_{12}$cycloalkoxy, halogen, carboxy, $C_1$–$C_7$alkoxycarbonyl, $C_3$–$C_{12}$cycloalkoxycarbonyl, cyano, trifluoromethyl, pentafluoroethyl, amino, N,N-mono- or N,N-di-$C_1$–$C_{20}$alkylamino or by nitro;

Q is —$SO_2$—; —O—; or —(CO)—;

X is —CH—; or —N—;

m is from 1 to 3; and t is 0 or 1;

and a cosmetically tolerable adjuvant.

23. An antimicrobial oral composition comprising from 0.01 to 15% by weight, based on the total weight of the composition, of a compound of formula (1) or (2) according to claim 22 and an orally tolerable adjuvant.

24. A pharmaceutical composition for the treatment of bacterial infections, comprising an antibacterially effective amount of a compound of formula (1) or (2) according to claim 22 and a therapeutically tolerable adjuvant.

25. A process for the preparation of a compound of formula (1) or (2) according to claim 1, wherein an indole compound (I), a keto or aldehyde compound of formula (II) and a dienophile of formula (IV) or (V), respectively, are reacted in a suitable solvent using an acid catalyst at a temperature of from 50° C. to 140° C. to form a compound of formula (1) or (2), respectively, in accordance with the following scheme:

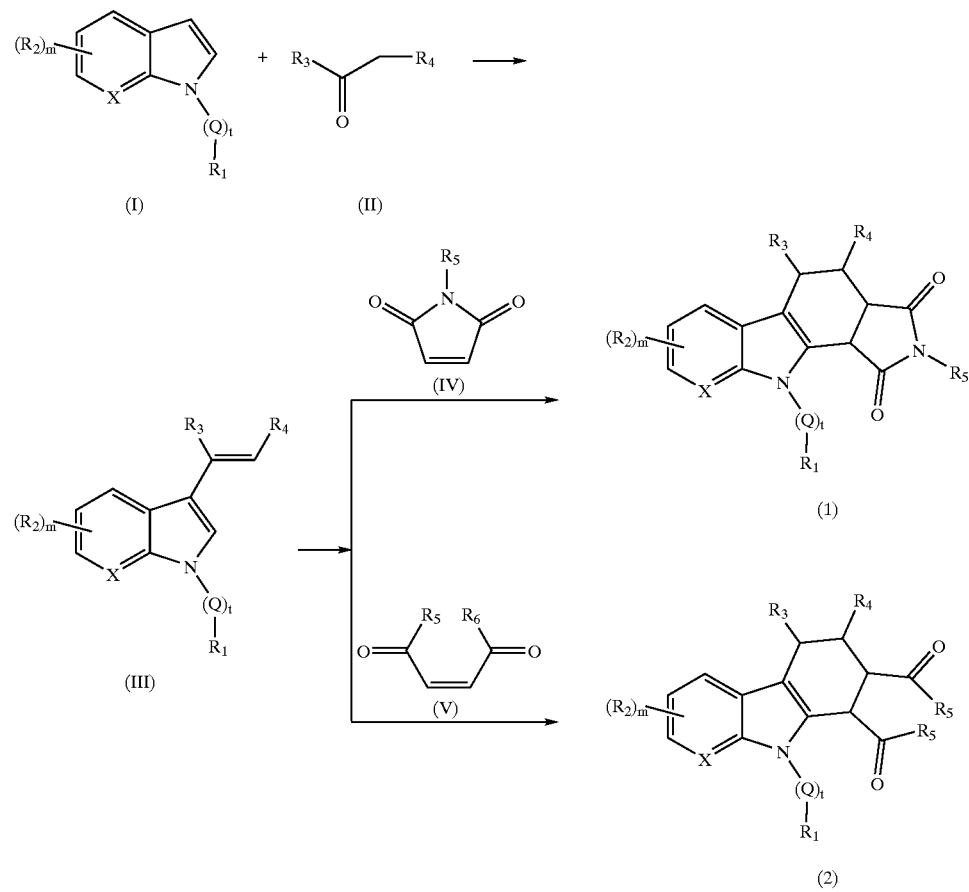
wherein $R_1$, $R_2$, $R_5$, $R_6$, m, Q, t and X are as defined in claim 1.